United States Patent [19]
Haynes et al.

[11] Patent Number: 5,863,540
[45] Date of Patent: Jan. 26, 1999

[54] ADHESION MOLECULE

[75] Inventors: Barton F. Haynes, Durham; Karen L. Patton, West Roxbury; Hua-Xin Liao, Chapel Hill, all of N.C.

[73] Assignee: Duke University, Durham, N.C.

[21] Appl. No.: 143,311

[22] Filed: Oct. 29, 1993

Related U.S. Application Data

[63] Continuation-in-part of Ser. No. 973,339, Oct. 30, 1992, abandoned, which is a continuation-in-part of Ser. No. 669,730, Mar. 15, 1991, abandoned.

[51] Int. Cl.$^6$ .......................... A61K 39/00; A61K 38/04; A61K 38/08; A61K 38/10
[52] U.S. Cl. ..................... 424/185.1; 424/184.1; 424/277.1; 514/2; 530/300; 530/324; 530/325; 530/326; 530/327; 530/328; 530/350; 530/380; 530/395; 530/827; 530/828; 530/829; 530/837; 530/838; 930/10
[58] Field of Search .............................. 424/184.1, 185.1, 424/277.1; 514/2; 530/300, 324–328, 350, 380, 395, 828, 827, 829, 837, 838; 930/10

[56] References Cited

U.S. PATENT DOCUMENTS

| | | |
|---|---|---|
| 5,002,873 | 3/1991 | St. John et al. . |
| 5,108,904 | 4/1992 | Landay . |

OTHER PUBLICATIONS

Avrameas, "Coupling of Enzymes to Proteins with Glutaraldehyde. Use of Conjugates for the Detection of Antigens and Antibodies", Immunochemistry 6:43–53 (1969).
Aruffo et al, "CD44 is the Principal Cell Surface Receptor for Hyaluronate", Cell 61:1303–1313 (1990).
Arch et al, "Participation in Normal Immune Responses of a Metastasis–Inducing Splice Variant of CD44", Science 257:682–685 (1992).
Kahn, "Adhesion Protein Studies Provide New Clue to Metastasis", Science 257:614 (1992).
Stamenkovic et al, "The hematopoietic and epithelial forms of CD44 are distinct polypeptides with different adhesion potentials for hyaluraonate–bearing cells", EMBO Journal 10(2):343–348 (1991).
Dougherty et al, Molecuelear Cloning of CD44R1 and CD44R2, Two Novel Isoforms of the Human CD44 Lymphocyte 'Homing' Receptor Expressed by Hemopoietic Cells, Terry Fox Lab. 15:54 (1991).
Gunthert et al, "A New Variant of Glycoprotein CD44 Confers Metastatic Potential to Rat Carcinoma Cells", Cell. 65:13–24 (1991).
Sy et al, "Distinct Effects of Two CD44 Isoforms on Tumor Growth In Vivo", J. Exp. Med. 174:859–866 (1991).
Hofmann et al, CD44 Splice Variants Confer Metastatic Behavior in Rats: Homologous Sequences Are Expressed in Human Tumor Cell Lines, Cancer Research 51:5292–5297 (1991).
Jackson et al, "Multiple Variants of the Human Lymphocyte Homing Receptor CD44 Generated by Insertions at a Single Site in the Extracellular Domain", J. of Biological Chemistry 267(7):4732–4739 (1992).
Goldstein et al, "A Human Lymphocyte Homing Receptor, the Hermes Antigen, is Related to Cartilage Proteoglycan Core and Link Proteins", Cell. 56:1063–1072 (1989).
Haynes et al, "CD44–A molecule involved in leukocyte adherence and T–cell activation", Immunology Today 10(12):423–428 (1989).
Wolffe et al, "The cDNA Sequence of Mouse Pgp–1 and Homolgoy to Hyman CD44 Cell Surface Antigen and Proteoglycan Core/Link Proteins", J. of Biological Chemistry 265(1):341–347 (1990).
Haynes et al, "The Transmembrane Hyaluronate Receptor (CD44): Multiple Functions, Multiple Forms", Cancer Cells 3(9):347–350 (1991).
Ware et al, "Characterization of the Surface Topograph and Putative Tertiary Structure of the Human CD7 Molecule", J. of Immunology 143(11):3632–3640 (1969).
Haynes et al, "Measurement of an Adhesion Molecule as an Indicator of Inflammatory Disease Activity", Arthritis and Rheumatism 34(11):1434–1443 (1991).
Culty et al, "The Hyaluronate Receptor is a Member of the CD44 (H–CAM) Family of Cell Surface Glycoproteins", The Journal of Cell Biology 111(6/Pt.1):27655–2774 (1990).
Lesley et al, "CD44 can be activated to function as an hyaluronic acid receptor in normal murine T cells", Eur. J. Immunol. 11:2719–2723 (1992).
Lesley et al, Binding of Hyaluronic Acid to Lymphoid Cell Lines Is Inhibited by Monoclonal Antibodies against Pgp–1 (Experimental Cell Research 187:224–233 (1990).
Miyake et al, "Hyaluronate Can Function as a Cell Adhesion Molecule and CD44 Participates in Hyaluronate Recognition", J. Exp. Med. 172:69–75 (1990).
Lesley et al, "Requirement for Hyaluronic Acid Binding by CD44: A Role for the Cytoplasmic Domain and Activation by Antibody", J. Exp. Med. 175:257–266 (1992).
Peach et al, "Identification of Hyaluronic Acid Binding Sites in the Extracellular Domain of CD44", The Journal of Cell Biology 122(1):257–264 (1993).
Goetinck et al, "The Tandemly Repeated Sequences of Cartilage Link Protein Contain the Sites for Interaction with Hyaluronic Acid", The Journal of Cell Biology 105:2403–2408 (1987).
He et al, "Molecular Isoforms of Murine CD44 and Evidence That the Membrane Proximal Domain Is Not Critical for Hyaluronate Recognition", The Journal of Cell Biology 119(6):1711–1719 (1992).

(List continued on next page.)

*Primary Examiner*—Anthony C. Caputa
*Attorney, Agent, or Firm*—Nixon & Vanderhye P.C.

[57] ABSTRACT

The present invention relates, in general, to a method of treating inflammation or inhibiting cancer cell metastasis. In particular, the present invention relates to a method of suppressing T cell activation, inhibiting CD44-mediated cell adhesion and CD44-monocyte IL1 release, treating inflammation, and transporting a drug to a site of inflammation.

13 Claims, 15 Drawing Sheets

OTHER PUBLICATIONS

Seiter et al, "Prevention of Tumor Metastasis Formation by Anti–Variant CD44", J. Exp. Med. 177:443–455 (1993).

Heider et al, "A Human Homologue of the Rat Metastasis–associated Variant of CD44 Is Expressed in Colorectal Carcinomas and Adenomatous Polyps", The Journal of Cell Biology 120(1):227–233 (1993).

Koopman et al, "Activated Human Lymphocytes and Agressive Non–Hodgkin's Lymphomas Express a Homologue of the Rat Metastasis–associated Variant of CD44", J. Exp. Med. 177:897–904 (1993).

Thomas et al, "CD44H Regulates Tumor Cell Migration on Hyaluronate–coated Substrate", The Journal of Cell Biology 118(4):971–977 (1992).

Turley et al, "Hyaluronan and a Cell–associated Hyaluronan Binding Protein Regulate the Locomotion of Ras–transformed Cells", The Journal of Cell Biology 112(5):1041–1047 (1991).

Kumar, V. et al. Proc. Natl. Acad. Sci USA 87:1337–1341, 1990.

Haynes, B.F. Springer Sum. Immunopatnol. 11:163–185, 1989.

Cohen, J. Science 262(5):841–843, Nov. 1993.

Picker et al, "Monoclonal Antibodies Against CD44[In-(Lu)–related p80], and Pgp–1 Antigens in Man Recognize the Hermes Class of Lymphocyte Homing Receptors", The Journal of Immunology 142(6):2046–2051 (1989).

Hale et al, "CD44 Antibody Against In(Lu)–Related p80, Lymphocyte–Homing Receptor Molecule Inhibits the Binding of Human Erythrocytes to T Cells", The Journal of Immunology 143(12):3944–3948 (1989).

Denning et al, "Antibodies Against the CD44 p80, Lymphocyte Homing Receptor Molecule Augment Human Peripheral Blood T Cell Activation", The Journal of Immunology 144(1):7–15 (1990).

Miyake et al, "Monoclonal Antibodies to Pgp–1/CD44 Block Lympho–Hemopoiesis in Long–Term Blone Marrow Cultures", 171:477–488 (1990).

Cohen, Jon, "Cancer Vaccines Get a Shot in the Arm", Science 262:841–843 (1993).

Haynes et al, "Differentiation of Human T Lymphocytes: 1. Acquisition of a Novel Human Cell Surface Protein (p80) During Normal Intrathymic T Cell Maturation", The Journal of Immunolgy 131(3):1195–1200 (1983).

Telen al, "Human Erythrocyte Antigens" Regulation of Expression of a Novel Erythrocyte Surface Antigen by the Inhibitor Lutheran In(Lu) Gene, J. Clin. Inves. 71:1878–1886 (1983).

"Biochemicals Organic Compounds for Research and Diagnostic Reagents" Sigma Catalog, pp. 1118–1119 (1992).

Fundamental Immunology, Third Edition, William E. Paul, M.D., Editor, Raven Press, New York, Ch. 8, p. 242.

Guo et al, "HIV–Induced Loss of CD44 Expression in Monocytic Cell Lines", The Journal of Immunology 151(4):2225–22236 (1993).

Rivadeneira et al, "Inhibition of HIV Type 1 Infection of Mononuclear Phagocytes by Anti–CD44 Antibodies", AIDS Research and Human Retroviruses 11(5):541–546 (1995).

Willerford et al, "Simian Immunodeficiency Virus is Restricted to a Subset of Blood CD4+ Lymphocytes that Includes Memory Cells", The Journal of Immunology 144(10):3779–3783 (1990).

Matsushita et al, "Selective Killing of HIV–Infected Cells by Anti–gp 120 Immunotoxins", AIDS Research and Human Retroviruses 6(2):193–203 (1990).

Nicholson et al, "In Vitro of Human Monocytes With Human T Lymphotropic Virus Type III/Lymphadenopathy–Associated Virus (HTLV–III/LAV)", The Journal of Immunology 137(1):323–329 (1986).

Hirsch et al, "Therapy for Human Immunodeficiency Virus Infection", The New England Journal of Medicine 1686–1695 (1993).

Fahey et al, "Status of immune–based therapies in HIV infection and AIDS", Clin. exp. Immunol. 88:1–5 (1992).

Edgington, Stephen M., "How Sweet It Is: Selectin–Mediating Drugs", Bio/Technology 10:383–389 (1992).

Shaffer, Marjorie, "Drug giants, start–ups target adhesion molecules, key to inflammatory disease", Biotechnology Newswatch, p. 9, Oct. 4, 1993.

Harris et al, "Therapeutic antibodies—the coming of age", TIBTECH 11:42–44 (1993).

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Cys  Glu  Lys  Asn  Gly  Arg  Tyr  Ser  Ile  Ser  Arg  Thr  Glu  Ala  Ala  Asp
1                   5                        10                           15
Cys  Cys  Lys  Ala  Phe  Asn
                    20
```

( 2 ) INFORMATION FOR SEQ ID NO:2:

( i ) SEQUENCE CHARACTERISTICS:
  ( A ) LENGTH: 23 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:2:

Cys Asn Thr Ser Gln Tyr Asp Thr Tyr Cys Phe Asn Ala Ser Ala Pro
1               5                   10                  15

Pro Glu Glu Asp Cys Thr Ser
            20

( 2 ) INFORMATION FOR SEQ ID NO:3:

( i ) SEQUENCE CHARACTERISTICS:
    ( A ) LENGTH: 32 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:3:

Cys Arg Asp Gly Thr Arg Tyr Val Gln Lys Gly Glu Tyr Arg Thr Asn
1               5                   10                  15

Pro Glu Asp Ile Tyr Pro Ser Asn Pro Thr Asp Asp Val Ser Ser
            20                  25                  30

( 2 ) INFORMATION FOR SEQ ID NO:4:

( i ) SEQUENCE CHARACTERISTICS:
    ( A ) LENGTH: 42 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:4:

Cys Arg Asp Gly Thr Arg Tyr Val Gln Lys Gly Glu Tyr Arg Ile Asn
1               5                   10                  15

Pro Glu Asp Ile Tyr Pro Ser Asn Pro Thr Asp Asp Val Ser Ser
            20                  25                  30

Gly Ser Ser Ser Glu Arg Ser Ser Thr Ser
35              40

( 2 ) INFORMATION FOR SEQ ID NO:5:

( i ) SEQUENCE CHARACTERISTICS:
    ( A ) LENGTH: 21 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:5:

Cys Tyr Arg Thr Asn Pro Glu Asp Ile Tyr Pro Ser Asn Pro Thr Asp
1               5                   10                  15

Asp Asp Val Ser Ser
            20

( 2 ) INFORMATION FOR SEQ ID NO:6:

(i) SEQUENCE CHARACTERISTICS:
    (A) LENGTH: 21 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:6:

Cys Thr Val His Pro Ile Pro Asp Glu Asp Ser Pro Trp Ile Thr Asp
1               5                   10                  15

Ser Thr Pro Arg Ile
            20

(2) INFORMATION FOR SEQ ID NO:7:

(i) SEQUENCE CHARACTERISTICS:
    (A) LENGTH: 20 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:7:

Asp Ser Pro Trp Ile Thr Asp Ser Thr Asp Arg Ile Pro Ala Thr Arg
1               5                   10                  15

Asp Gln Asp Thr
            20

(2) INFORMATION FOR SEQ ID NO:8:

(i) SEQUENCE CHARACTERISTICS:
    (A) LENGTH: 36 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:8:

Cys Ala Thr Arg Asp Gln Asp Thr Phe His Pro Ser Gly Gly Ser His
1               5                   10                  15

Thr Thr His Glu Ser Glu Ser Asp Gly His Ser His Gly Ser Gln Glu
            20                  25                  30

Gly Gly Ala Asn
        35

(2) INFORMATION FOR SEQ ID NO:9:

(i) SEQUENCE CHARACTERISTICS:
    (A) LENGTH: 30 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:9:

Cys Arg Asp Gly Ile Arg Tyr Val Gln Lys Gly Glu Tyr Pro Ser Asn
1               5                   10                  15

Pro Thr Asp Asp Thr Ser Gly Gly Tyr Ile Phe Tyr Thr Phe
            20                  25                  30

(2) INFORMATION FOR SEQ ID NO:10:

(i) SEQUENCE CHARACTERISTICS:

(A) LENGTH: 31 amino acids
              (B) TYPE: amino acid
              (C) STRANDEDNESS: single
              (D) TOPOLOGY: linear (ii) MOLECULE TYPE: peptide (xi) SEQUENCE DESCRIPTION: SEQ ID NO:10:

Leu  Cys  Leu  Val  Pro  Leu  Ser  Leu  Ala  Gln  Ile  Asp  Leu  Asn  Ile  Thr
1                   5                        10                       15

Cys  Arg  Phe  Ala  Gly  Val  Phe  His  Val  Glu  Lys  Asn  Gly  Arg  Tyr
                20                       25                       30

(2) INFORMATION FOR SEQ ID NO:11:

(i) SEQUENCE CHARACTERISTICS:
              (A) LENGTH: 28 amino acids
              (B) TYPE: amino acid
              (C) STRANDEDNESS: single
              (D) TOPOLOGY: linear (ii) MOLECULE TYPE: peptide (xi) SEQUENCE DESCRIPTION: SEQ ID NO:11:

Leu  Cys  Lys  Ala  Phe  Asn  Ser  Thr  Leu  Pro  Thr  Met  Ala  Gln  Met  Glu
1                   5                        10                       15

Lys  Ala  Leu  Ser  Ile  Gly  Phe  Glu  Thr  Cys  Arg  Tyr
                20                       25

(2) INFORMATION FOR SEQ ID NO:12:

(i) SEQUENCE CHARACTERISTICS:
              (A) LENGTH: 21 amino acids
              (B) TYPE: amino acid
              (C) STRANDEDNESS: single
              (D) TOPOLOGY: linear (ii) MOLECULE TYPE: peptide (xi) SEQUENCE DESCRIPTION: SEQ ID NO:12:

Cys  Arg  Tyr  Gly  Phe  Ile  Glu  Gly  His  Val  Val  Ile  Pro  Arg  Ile  His
1                   5                        10                       15

Pro  Asn  Ser  Ile  Cys
                20

(2) INFORMATION FOR SEQ ID NO:13:

(i) SEQUENCE CHARACTERISTICS:
              (A) LENGTH: 19 amino acids
              (B) TYPE: amino acid
              (C) STRANDEDNESS: single
              (D) TOPOLOGY: linear (ii) MOLECULE TYPE: peptide (xi) SEQUENCE DESCRIPTION: SEQ ID NO:13:

Arg  Tyr  Gly  Phe  Ile  Glu  Gly  His  Val  Val  Ile  Pro  Arg  Ile  His  Pro
1                   5                        10                       15

Asn  Ser  Ile (2) INFORMATION FOR SEQ ID NO:14:

(i) SEQUENCE CHARACTERISTICS:
              (A) LENGTH: 11 amino acids
              (B) TYPE: amino acid
              (C) STRANDEDNESS: single
              (D) TOPOLOGY: linear (i i) MOLECULE TYPE: peptide (x i) SEQUENCE DESCRIPTION: SEQ ID NO:14:

Leu Thr Tyr Asn Thr Ser Gln Tyr Asp Thr Tyr
1               5                   10

(2) INFORMATION FOR SEQ ID NO:15:

(i) SEQUENCE CHARACTERISTICS:
      (A) LENGTH: 29 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:15:

Cys Arg Thr Asn Met Asp Ser Ser His Ser Thr Thr Leu Gln Pro Thr
1               5                   10                  15

Ala Asn Pro Asn Thr Gly Leu Val Glu Asp Leu Asp Arg
                20                  25

(2) INFORMATION FOR SEQ ID NO:16:

(i) SEQUENCE CHARACTERISTICS:
      (A) LENGTH: 30 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:16:

Cys Thr Gly Pro Leu Ser Met Thr Thr Gln Gln Ser Asn Ser Gln Ser
1               5                   10                  15

Phe Ser Thr Ser His Glu Gly Leu Glu Glu Asp Lys Asp His
                20                  25                  30

(2) INFORMATION FOR SEQ ID NO:17:

(i) SEQUENCE CHARACTERISTICS:
      (A) LENGTH: 28 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:17:

Cys Pro Thr Thr Ser Thr Leu Thr Ser Ser Asn Arg Asn Asp Val Thr
1               5                   10                  15

Gly Gly Arg Arg Asp Pro Asn His Ser Glu Gly Ser
                20                  25

(2) INFORMATION FOR SEQ ID NO:18:

(i) SEQUENCE CHARACTERISTICS:
      (A) LENGTH: 19 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:18:

Cys Asn Arg Asn Asp Val Thr Gly Gly Arg Arg Asp Pro Asn His Ser
1               5                   10                  15

Glu Gly Ser ( 2 ) INFORMATION FOR SEQ ID NO:19:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

```
Cys Thr His Leu Leu Glu Gly Tyr Thr Ser His Tyr Pro His Thr Lys
1               5                   10                  15
Glu Ser Arg Thr Phe Ile Pro Val Thr Ser Ala Lys
            20                  25
```

( 2 ) INFORMATION FOR SEQ ID NO:20:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:20:

```
Cys Thr Gly Ser Phe Gly Val Thr Ala Val Thr Val Gly Asp Ser Asn
1               5                   10                  15
Ser Asn Val Asn Arg Ser Leu
            20
```

( 2 ) INFORMATION FOR SEQ ID NO:21:

( i ) SEQUENCE CHARACTERISTICS:
        ( A ) LENGTH: 25 nucleic acids
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

GGATCTAGAT TACACCCCAA TCTTC                                    25

( 2 ) INFORMATION FOR SEQ ID NO:22:

( i ) SEQUENCE CHARACTERISTICS:
        ( A ) LENGTH: 29 nucleic acids
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

GCCAAGCTTC CACCATGGAC AAGTTTTGG                              29

( 2 ) INFORMATION FOR SEQ ID NO:23:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:23:

Met Asp Lys Phe Trp Trp
1               5

( 2 ) INFORMATION FOR SEQ ID NO:24:

( i ) SEQUENCE CHARACTERISTICS:
      ( A ) LENGTH: 5 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:24:

Arg Leu Arg Val Pro
1               5

( 2 ) INFORMATION FOR SEQ ID NO:25:

( i ) SEQUENCE CHARACTERISTICS:
      ( A ) LENGTH: 41 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:25:

Met Asp Lys Phe Trp Trp His Ala Ala Trp Gly Leu Cys Leu Val Pro
1               5                   10                  15

Leu Ser Leu Ala Gln Ile Asp Leu Asn Thr Cys Arg Phe Ala Gly Val
            20              25                  30

Phe His Val Glu Lys Asn Gly Arg Tyr
35              40

( 2 ) INFORMATION FOR SEQ ID NO:26:

( i ) SEQUENCE CHARACTERISTICS:
      ( A ) LENGTH: 25 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:26:

Met Asp Lys Phe Trp Trp His Ala Ala Trp Gly Leu Cys Leu Leu Gln
1               5                   10                  15

Leu Ser Leu Ala Gln Ile Asp Leu Asn
            20              25

( 2 ) INFORMATION FOR SEQ ID NO:27:

( i ) SEQUENCE CHARACTERISTICS:
      ( A ) LENGTH: 25 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:27:

Met Asp Lys Phe Trp Trp His Ala Ala Trp Gly Leu Cys Leu Val Pro
1               5                   10                  15

Leu Ser Leu Ala Gln Ile Asp Leu Asn
            20              25

( 2 ) INFORMATION FOR SEQ ID NO:28:

-continued (i) SEQUENCE CHARACTERISTICS:
    (A) LENGTH: 10 amino acids
    (B) TYPE: amino acid
    (D) TOPOLOGY: linear (ii) MOLECULE TYPE: peptide (xi) SEQUENCE DESCRIPTION: SEQ ID NO:28:

Arg Leu Arg Val Pro Gln Ile Asp Leu Asn
1               5                   10

ADHESION MOLECULE

This application is a continuation-in-part of application Ser. No. 07/973,339, filed Oct. 30, 1992, (now abandoned), which is a continuation-in-part of application Ser. No. 07/669,730, filed Mar. 15, 1991, now abandoned, the entire contents of both applications being incorporated herein by reference.

This invention was made with Government support under Grant No. AR 39162 awarded by the National Institutes of Health. The Government may have certain rights in this invention.

BACKGROUND OF THE INVENTION

1. Field of the Invention

The present invention relates to methods of suppressing T cell activation, inhibiting CD44-mediated cell adhesion and CD44-monocyte IL1 release, treating inflammation, and transporting a drug or cytotoxic agent to a site of inflammation.

2. Background Information

Recent work has defined the importance of cell adhesion molecules in immune cell function (reviewed in Springer (1990) Nature 346:425–434; Haynes et al. (1989) Springer Sem. Immunopathol. 11:163–185; Hemler (1988) Immunol. Today 109–113). Cell adhesion molecules have been described that are receptors for soluble molecules (Haynes et al (1984) Nature 312:763–766), receptors for viruses (reviewed in Springer (1990) Nature 346:425–434; Dalgleish et al. (1984) Nature 312:763–766; Klatzmann et al. (1984) Science 225:59–63), and ligands for other cell surface molecules (reviewed in Springer (1990) Nature 346:425–434; Haynes et al. (1989) Springer Sem. Immunopathol. 11:163–185; Hemler (1988) Immunol. Today 109–113).

On immune cells, cell adhesion molecules mediate a wide variety of normal cell functions including cell movement, adherence to other cells, adherence to extracellular matrix proteins, mononuclear cell homing and monocyte cytokine release (reviewed in Springer (1990) Nature 346:425–434; Haynes et al. (1989) Springer Sem. Immunopathol. 11:163–185; Hemler (1988) Immunol. Today 109–113; Haynes et al. (1989) Immuno. Today 10:423–428). The CD44 molecule has been of recent interest because this protein has multiple proinflammatory functions, exists in soluble form in serum and plasma, and regulates the function of other adhesion molecules (reviewed in Haynes et al. (1989) Springer Sem. Immunopathol. 11:163–185; Haynes et al. (1989) Immuno. Today 10:423–428).

The CD44 molecule is an 85kd glycosylated molecule with N-terminal sequence homology to cartilage link proteins (Stamenkovic et al. (1989) Cell 56:1057–1062; Goldstein et al. (1989) Cell 56:1063–1072). Forms of CD44 of varying sizes have been described on many cell types (Haynes et al. (1989) Immunol. Today 10:423–428, Stamenkovic et al. (1989) Cell 56:1057–1062; Goldstein et al. (1989) Cell 56:1063–1072; Jalkanan et al. (1988) J. Immunol. 141:1615–1623). Variations in the size of CD44 isoforms have been suggested to be due to glycosylation differences, the addition of chondroitin sulfate molecules to CD44 (Jalkanan et al. (1988) J. Immunol. 141:1615–1623), and in some cases, to alternative splicing of CD44 mRNA (Dougherty et al. (1988) Exp. Hemat. 18:703, St. John et al. (1989) Req. Immunol. 300–310). Three forms of CD44 have been identified on peripheral blood mononuclear cells (PBMC) (Hale et al.) and an 85kd form (presumably a secreted form) has been identified in serum, plasma (Telen et al. (1983) J. Clin. Invest. 71:1878–1886; Lucas et al. (1989) Blood 73:596–600) and now synovial fluid.

CD44H is the hematopoietic form of the molecule, and additional forms are created by alternative splicing and insertion of up to 5 additional domains (Stamenkovic et al. EMBO J. (1991)10:343–348; Gunthert et al. Cell (1991) 65:13–24; Dougherty et al. J. Exp. Med. (1991) 174:1–5; Hoffman et al. Cancer Res. (1991) 51:5292–5297; Jackson et al. J. Biol. Chem. (1992) 267:1432–1439).

Functionally, the CD44 molecule has been shown to be a central molecule involved in T lymphocyte adhesion, T lymphocyte activation and monocyte cytokine release (Haynes et al. (1989) Immunol. Today 10:423–428; Jalkanen et al. (1986) Science 233:556–558; Jalkanen et al. (1987) J. Cell Biol. 983–990; Aruffo et al. (1990) Cell 61:1303–1313; Miyake et al. (1990) J. Exp. Med. 172:69–75; Lesley et al. (1990) Exp. Cell Res. 187:224–233; Stamenkovic et al. (1989) Cell 56:1057–1062; Goldstein et al. (1989) Cell 56:1063–1072; Jalkanan et al. (1988) J. Immunol. 141:1615–1623). The association of the CD44 intracellular domain with the cytoskeletal protein, ankyrin, and with the enzyme protein kinase C (PKC) (Kalomiris et al. (1989) J. Biol. Chem. 264:8113–8119) has suggested a role for CD44 in signal transduction of surface events to intracellular molecules. Ligand binding to the CD44 molecule promotes T cell adherence to monocytes via other adhesion molecule pathways (ICAM-1/LFA-1 and LFA-3/CD2) (Denning et al.; Koopman et al (1990) J. Immunol. 145:3589–3593) suggesting that CD44 can serve as a regulator of function of other adhesion molecules (reviewed in Haynes et al. (1989) Springer Sem. Immunopathol. 11:163–185; Haynes et al. (1989) Immunol. Today 109–113).

Recent studies have demonstrated that the CD44 protein is the primary receptor for hyaluronate in rodents and humans (Aruffo et al. (1990) Cell 61:1303–1313; Miyake et al. (1990) J. Exp. Med. 172:69–75; Lesley et al. (1990) Exp. Cell Res. 187:224–233). Both hyaluronate (Hiro et al. (1986) Biochem. Biophys. Res. Comm. 715–722) and CD44 mAB (Webb et al. Science, 249:1295) binding to monocytes induces monocyte IL1 release. On T cells, hyaluronate and CD44 mAB ligation of CD44 have disparate effects; CD44 mABs augment T cell triggering (Huet et al. (1989) J. Immunol. 798–801; Shimuzu et al. (1989) J. Immunol. 143:2457–2463) while hyaluronate suppresses T cell triggering (Anastassiades et al. (1984) Rheumatol. 11:734–729). Finally, CD44 mabs and polyclonal anti-CD44 serum have been shown to inhibit the binding of lymphocytes to high endothelial venules in inflammatory sites such as synovium (Jalkanen et al. (1986) Science 233:556–558; Jalkanen et al. (1987) J. Cell Biol. 983–990; Jalkanan et al. (1988) J. Immunol. 141:1615–1623), suggesting lymphocyte CD44 is one of several molecules involved in organ-specific lymphocyte homing. Thus, the hyaluronate receptor (CD44) molecule, by existing in several isoforms, and by virtue of wide cellular distribution, functional association with other adhesion molecules, and physical association with ankryin and PKC, is a multifunctional proinflammatory molecule involved in immune cell activation (reviewed in Haynes et al. (1989) Immunol. Today 10:423–428) as well as metastasis of certain tumor cell types (reviewed in Haynes et al. (1991) Cancer Cells 3:347–350).

Hyaluronate, the ligand for CD44, is an important component of synovial fluid and plays a critical role in maintaining high viscosity of synovial fluid in normal diarthroidal joints (reviewed in Schuber and Hammerman (1964)

Bull. Rheum. Dis. 14:345–348; Castor et al. (1966) Arth. Rheum. 9:783–794). In rheumatoid arthritis (RA) synovial fluid, hyaluronate concentration and degree of polymerization is decreased (Castor et al. (1966) Arth. Rheum. 9:783–794). Reduction in synovial fluid hyaluronate concentration and degree of polymerization has been suggested to be an important factor leading to joint dysfunction and destruction in RA (Schubert et al. (1964) Bull. Rheum. Dis. 14:345–348; Castor et al. (1966) Arth. Rheum. 9:783–794), and potentially may decrease the immunosuppressive effect of hyaluronate on T cells (Anastassiades et al. (1984) Rheumatol. 11:734–729).

Applicants have demonstrated that CD44 is upregulated in RA on many synovial cell types and that the level of CD44 present in synovial tissue is directly proportional to the degree of synovial inflammation in RA. Applicants have also demonstrated that CD44 is immunosuppressive to T cells. The present invention relates, at least in part, to a method of interdiction of proinflammatory functions of the CD44 molecule.

SUMMARY OF THE INVENTION

It is a general object of this invention to provide a method of treating inflammation.

It is a specific object of this invention to provide a method of suppressing T cell activation.

It is another object of the invention to provide a method of inhibiting CD44-mediated cell adhesion or CD44-mediated monocyte IL1 release.

It is yet another object of the invention to provide a method of transporting a drug or cytotoxic agent to a site of inflammation, and to compositions suitable for use in such a method.

It is a further object of the invention to provide peptides of CD44 and antibodies against these peptides.

It is another object of the present invention to provide a method to determine the metastatic potential of hematopoietic cell types.

It is a further object of the present invention to provide a test kit for determining the metastatic potential of hematopoietic cell types.

Further objects and advantages of the present invention will be clear from the description that follows.

In one embodiment, the present invention relates to a method of suppressing T cell activation in an human comprising administering to the human CD44 protein peptide or derivative thereof in an amount sufficient to suppress T cell activation.

In another embodiment, the present invention relates to a method of inhibiting CD44-mediated cell adhesion or CD44-mediated monocyte IL1 release in an animal comprising administering to the human CD44 protein or peptide or derivative thereof in an amount sufficient to inhibit CD44-mediated cell adhesion or CD44-monocyte IL1 release.

In a further embodiment, the present invention relates to a method of treating inflammation in an human comprising administering to the human CD44 protein or peptide or derivative thereof in an amount sufficient to reduce the inflammation.

In another embodiment, the present invention relates to a method of transporting a drug or cytotoxic agent to a site of inflammation in an human comprising administering to the human CD44 protein or peptide or derivative thereof linked to the drug or cytotoxic agent. In a preferred embodiment, the CD44 protein or peptide or derivative thereof and the drug or cytotoxic agent are incorporated into a liposome.

In yet another embodiment, the present invention relates to a method of inhibiting T-cell function in a human comprising administering to the human antibodies against CD44, preferably antibodies against CD44H or CD44E or portion or derivative thereof in an amount sufficient to inhibit T-cell function.

In a further embodiment, the present invention relates to a method of determining the metastatic potential of hematopoietic cell types comprising contacting test cells with antibodies against synthetic peptides of CD44H or CD44E, separately or together, and measuring the amount of binding between the cells and the antibodies.

In another embodiment, the present invention relates to a peptide represented by any one of SEQ ID NO:1–28.

In further embodiment, the present invention relates to a peptide having the sequence set forth in SEQ ID NO:25 or SEQ ID NO:26 or portion thereof that includes at least the sequence set forth in SEQ ID NO:23.

In yet another embodiment, the present invention relates to a hybridoma cell that produces an antibody having the characteristics of 5F12, ATCC deposit no. HB11480.

In a further embodiment, the present invention relates to a method of inhibiting binding of hyaluronan to a molecule of CD44 comprising contacting the molecule of CD44 with at least one peptide represented in SEQ ID NO:3, SEQ ID NO:4, SEQ ID NO:5, SEQ ID NO:8, SEQ ID NO:9 or SEQ ID NO:25 or SEQ ID NO:26, or portion thereof that includes at least SEQ ID NO:23, under conditions such that the binding is inhibited.

In another embodiment, the present invention relates to a method of inhibiting binding of hyaluronan to a molecule of CD44 comprising contacting the hyaluronan with a CD44 mimetope recognized by the antigen binding site of the Fab fragment of antibody 5F12 under conditions such that the binding is inhibited.

BRIEF DESCRIPTION OF THE DRAWINGS

FIGS. 1A, B, and C are from trauma synovium no. 229 (inflammation score=5). Panel A shows hematoxylin and eosin (H and E) stain, panel B shows reactivity of synovium with anti-fibronectin mAb FN1S (fibronectin index=2+) and panel C shows reactivity of synovium with anti-CD44 mAb AlG3 (CD44 index=1+). FIGS. 1D, E, and F are from OA synovium no. 36 (inflammation score=5). Panel D shows H and E stain, panel E shows fibronectin expression (fibronectin index=1+), and panel F shows CD44 expression (CD44 index=1+). FIGS. 1G, H, and I are from RA no. 86 (inflammation score=18). Panel G shows H and E stain, panel H shows fibronectin expression (fibronectin index= 4+) and panel I shows CD44 expression (CD44 index=3+). FIGS. 1J, K, and L show RA synovium no. 7 (inflammation score=13) with pannus formation. FIG. 1J shows H and E stain, FIG. 1K shows fibronectin expression (fibronectin index=4+) and FIG. 1L shows CD44 expression (CD44 index=4+). All panels showing fibronectin and CD44 expression are indirect IF. All panels 400X.

FIG. 2A shows Western blot of OA synovium no. 198

(inflammation score=3), trauma synovium no. 229 (inflammation score=5), and RA synovium nos. 7, 154, and 86 (inflammation scores 13, 21, and 18, respectively). FIG. 2B shows the area under the densitometry curve (arbitrary units) of the CD44 bands shown in FIG. 2A.

FIG. 5A compares CD44 levels in gout versus trauma synovial fluid. Control lanes A and B as in FIG. 3. Lane B shows CD44 in fluid 11 (CD44 level=1.0) and lane D shows CD44 in fluid32 (CD44 level=3.79). Band at 40 kd in lanes A, B, and C is a non-specific band not present in lane D for technical reasons. FIG. 5B compares CD44 levels in psoriatic arthritis versus trauma synovial fluid. Control lanes A and C as in FIG. 3. Lane B is trauma fluid no. 11 (CD44 level=1.0) lane D is psoriatic arthritis synovial fluid no. 100 (CD44 level=7.0).

DETAILED DESCRIPTION OF THE INVENTION

Figure 1A:
FIGS. 1A–1L. Upregulation of CD44 Expression in RA But Not in Non-inflammatory OA or Trauma.
Figure 1B:
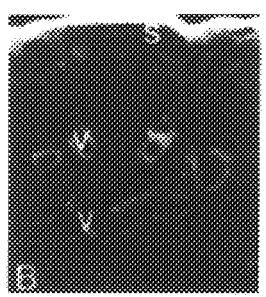
Figure 1C:
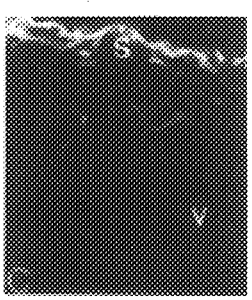
Figure 1D:
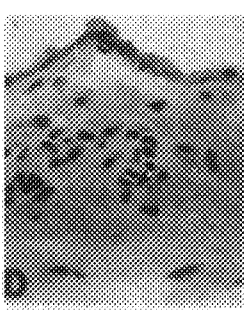
Figure 1E:
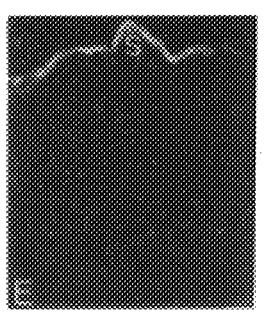
Figure 1F:
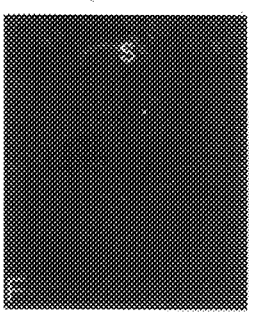

The present invention relates to a method of treating inflammation and immune-mediated tissue damage, such as occurs, for example, in the course of autoimmune diseases.

In one embodiment, the present invention relates to a method of suppressing T cell activation in an human comprising administering to the human the CD44 protein, or derivative or peptide portion thereof, in an amount sufficient to effect suppression. Examples of CD44 peptides (CD44H form) suitable for use in the present method include those set forth in Table 1. Peptides from the CD44E form, containing domains 4 and 5, are also suitable for use in the present invention and are set forth in Table 2.

TABLE 1

Examples of CD44 Peptides That Can Be Used To Inhibit C44-Mediated Immune Cell Functions

| Peptide | Sequence | aa. no. | SEQ ID NO: |
| --- | --- | --- | --- |
| CD44-1 | (C)EKNGRYSISRTEAADCCKAFN | 37–57 | 1 |
| CD44-2 | (C)NTSQYDTYCFNASAPPEEDCTS | 110–131 | 2 |
| CD44-3 | (C)RDGTRYVQKGEYRTNPEDIYPS NPTDDDVSS | 150–180 | 3 |
| CD44-4 | (C)RDGTRYVQKGEYRINPEDIYPS NPTDDDVSSGSSSERSSTS | 150–190 | 4 |
| CD44-5 | (C)YRTNPEDIYPSNPTDDDVSS | 161–180 | 5 |
| CD44-6 | (C)TVHPIPDEDSPWITDSTPRI | 200–219 | 6 |
| CD44-6A | DSPWITDSTDRIPATRDQDT | 208–227 | 7 |
| CD44-7 | (C)ATRDQDTFHPSGGSHTTHESES DGHSHGSQEGGAN | 221–255 | 8 |

TABLE 1-continued

Examples of CD44 Peptides That Can Be Used To
Inhibit C44-Mediated Immune Cell Functions

| Peptide | Sequence | aa. no. | SEQ ID NO: |
|---|---|---|---|
| CD44-8 | (C)RDGIRYVQKGEY-PSNPTDD-T SGGYIFYTF | 150–161, 170–177, 189–198 | 9 |
| CD44-9 | LCLVPLSLAQIDLNITCRFAGVFHV EKNGRY | 12–42 | 10 |
| CD44-10 | LCKAFNSTLPTMAQMEKALSIGFET CRY | 52–79 | 11 |
| CD44-11 | CRYGFIEGHVVIPRIHPNSIC | 77–97 | 12 |
| CD44-12 | RYGFIEGHVVIPRIHPNSI | 76–96 | 13 |
| CD44-13 | LTYNTSQYDTY | 107–117 | 14 |

Sequences from Stamenkovic et al., Cell (1989) 56:1057–1062.

TABLE 2

Peptides of CD44R1 and CD44R2 Inserts

| Peptides | Sequences | aa. no. | SEQ ID NO: |
|---|---|---|---|
| CD44-17 | (C)RTNMDSSHSTTLQPTANPNTGLVEDLDR | 221–248 | 15 |
| CD44-18 | (C)TGPLSMTTQQSNSQSFSTSHEGLEEDKDH | 249–277 | 16 |
| CD44-19 | (C)PTTSTLTSSNRNDVTGGRRDPNHSEGS | 278–304 | 17 |
| CD44-19A | (C)NRNDVTGGRRDPNHSEGS | 287–304 | 18 |
| CD44-20 | (C)THLLEGYTSHYPHTKESRTFIPVTSAK | 305–331 | 19 |
| CD44-21 | (C)TGSFGVTAVTVGDSNSNVNRSL | 332–353 | 20 |

Sequences are from Stamenkovic et al. (1991) EMBO J. 10:343–348.

The CD44-6A peptide contains an ala-thr-arg (ATR) sequence that is deleted in the process of splicing in various inserts to form CD44 splice variants. Antibodies that include the ATR sequence as targets for antibody responses will be CD44H specific, since the splice variants do not contain the ATR sequence.

Administration of the proteins/peptides of the invention can be by injection or topical application (for example topically applied to the eye). Injection can be made directly into a skin lesion.

An additional form of the CD44 molecule that may be used as an immunosuppressive agent is a recombinantly produced CD44 molecule or a portion of the CD44 molecule produced by recombinant DNA technology. An example of such a form of CD44 has been reported by Aruffo et al. Cell (1990) 61:1303–1313. This form of CD44 has been recombinately engineered to contain portions of the immunoglobulin protein constant domains. The addition of immunoglobulin domains to the extracellular domain of CD44 yielded in molecule called CD44-Rg-2 that has the properties of being secluded by COS cells when a plasmid containing this CD44-Rg2 gene was transfected into COS cells (Aruffo et al. Cell (1990) 61:1303–1313). The presence of immunoglobulin on the extracellular domain of CD44 would also have the potential advantage of increasing the circulating half-life of the CD44 molecule when administered to humans or animals.

Production of CD44-Rg-2 fusion construct: CD44-Rg-2 plasmid can be transfected into COS cells using DEAE dextran as described in Seed PNAS (1987) 84:3365–3369, and Aruffo, et al. Cell (1990) 61:1303–1313, 1990. Semiconfluent COS cells plated on 100 mm plates will be transfected. Twelve hours after transfection, cells are trypsinized, seeded onto fresh 100 mm dishes and allowed to grow for 7–10 days. On the fourth day 5 ml fresh media, 10% calf serum are added per dish. Supernatants are harvested and stored at 4° C.

Purification of CD44-Rg protein: Twelve hours following transfection, a fraction of the COS cells transfected are seeded into flasks. Thirty-six hours post-transfection, the cells are washed with PBS and overlayed with cystein-methionine media for 30 min. [$^{35}$Methionine and [$^{35}$S] Methionine and [$^{35}$] Cysteine will be added to a final concentration of 150 $\mu$Cl/ml, and the cells will be allowed to incorporate the label overnight. The supernatants will be harvested and incubated with 200 $\mu$l of protein A-Trisacryl at 4° C. for 12 hours. The beads will be collected by centrifugation and washed in 10 ml of PBS, 1 Nonidet P-40. The beads will then be eluted 200 $\mu$l of 1% SDS.

In another embodiment, the present invention relates to a method of inhibiting various types of cellular interactions including macrophage T cell interactions and lymphocyte and macrophage interactions with endothelial cells. The invention further relates to a method of inhibiting CD44-monocyte IL1 release. These methods also involve the administration of an effective amount of the CD44 protein or derivative or portion thereof to an animal in need of such treatment.

CD44 protein suitable for use in the present invention can be isolated from synovial tissue (preferably, human synovial tissue) or the protein can be produced recombinantly. Synthetic peptides reflective of discrete regions of the CD44 molecule can be made by standard techniques. Antibodies (monoclonal or polyclonal) against discrete regions of the CD44 molecule (for example, those shown in Tables 1 and 2) may be made by known methods and may be tagged with markers (e.g., fluorescent, radioactive, etc.) by means known in the art.

One skilled in the art will appreciate that the amounts to be administered for any particular treatment protocol can readily be determined. The CD44 protein, peptide or derivative can be administered together with a pharmaceutically acceptable carrier.

In yet another embodiment, the present invention relates to a method of transporting a drug or cytotoxic agent to a site of inflammation in an animal comprising administering to the animal the CD44 protein, or peptide or derivative thereof, linked, preferably covalently, to the drug or cytotoxic agent.

Examples of drugs to be targeted to organ-specific sites of inflammation are non-steroidal anti-inflammatory agents, forms of glucocorticosteroids, and cytoxic agents such as cyclophosphamide. By either incorporating these agents in liposomes bearing CD44 molecules, or by physically linking CD44 molecules to these drugs, one could achieve selective targeting or homing of the drug-CD44 complexes to sites of upregulated CD44 expression, that is sites of inflammation.

In a further embodiment, the present invention relates to a method of transporting a drug or cytotoxic agent to a site of inflammation in an animal comprising administering to the animal CD44 protein, or peptide or derivative thereof, and a drug or cytotoxic agent wherein both are incorporated into a liposome.

In another embodiment, the present invention relates to a method of inhibiting T cell function in a human comprising administering to the human antibodies against CD44, preferably CD44H or CD44E peptides, in an amount sufficient to inhibit T cell function.

In yet another embodiment, antibodies against the CD44-6A or the CD44-19A peptides (either polyclonal or monoclonal) can be used in vivo as immunotherapeutic agents to inhibit T cell function in the therapy of autoimmune or inflammatory disease. Arch et al., Science (1992) 257:682–685, have demonstrated that a rodent monoclonal antibody (1.1ASML) against a rat CD44 isoform containing domain 3 of CD44 insert (Hoffman et al. Cancer Res. (1991) 51:5292–5297) will inhibit the in vivo activation of T and B cells. Mab 1.1ASML reacts with a different CD44 sequence than CD44-6A or CD44-19A peptides.

In a further embodiment, the present invention relates to a method of determining the metastatic potential of hematopoietic cell types comprising contacting test cells with antibodies (which may be attached to markers) against CD44, preferably antibodies against CD44H or CD44E peptides, most preferably antibodies against CD44-6A or CD44-19A peptides, either alone or together, and measuring the amount of binding between the cells and the antibodies by, for example, fluorescent or radioactive means. One skilled in the art will appreciate that such a method may be used in vitro as well as in vivo.

In another embodiment, antibodies against the CD44-6A or the CD44-19A peptides can be used to make monoclonal or polyclonal antibodies that are specific for cells that express these isoforms of CD44. For example, Sy et al. J. Exp. Med. (1991) 174:859–866, have demonstrated that the CD44H isoform confers the ability to metastasize to B cell lymphoma cells, while the CD44E(R1) form does not. Thus, CD44H specific antisera can be used to determine the metastatic potential of malignant hematopoietic cell types. Similarly, anti-CD44-19A monoclonal or polyclonal antibodies raised against the CD44-19A peptide can be used to identify cells that mediate functions associated with expression of CD44 domains 4 or 5, such as metastasis of a particular cell type.

One skilled in the art will appreciate that CD44 peptides and anti-sera such as CD44-6A peptide or anti-CD44-6A polyclonal or monoclonal antisera can be used to treat hematopoietic malignancies in vivo that involve CD44H+ cells. Alternatively, anti-CD44-6A anti-sera can be used to purge bone marrow in vitro to rid bone marrow of CD44H+ malignant cells.

In a further embodiment, the present invention relates to methods of inhibiting CD44-hyluronan (HA) interaction and to compounds suitable for use in such a method. CD44 ligation of HA is involved in a variety of pathologic clinical situations. Gunthert et al (Cell 65:13 (1991)) have shown that a splice variant of CD44 is requred to be expressed for adenocarcinoma cells to metastasize. A mab against this CD44 variant prevents metastasis of adenocarcinoma cells (Seiter et al, J. Exp. Med. 177:443 (1993)), and a human homologue of this CD44 variant is expressed in human colorectal carcinomas (Heider et al, J. Cell. Biol. 120:227 (1993)), on aggressive non-Hodgkin's lymphomas (Koopman et al, J. Exp. Med. 177:897 (1993)), and on metastatic (but not on non-metastatic) human melanoma cells (Thomas et al, J. Cell. Biol. 118:971 (1992)). CD44 expression is upregulated on ras transformed tumor cells (Thomas et al, J. Cell. Biol. 118:971 (1992); Turley et al, J. Cell. Biol. 112:1041 (1991)), and HA ligation of tumor CD44 molecules is essential for tumor cell migration (Turley et al, J. Cell. Biol. 112:1041 (1991)). Transfection of CD44H into human B cell lymphoma cells conferred on the B cell lymphomas the ability to metastasize (Sy et al, J. Exp. Med. 174:859 (1991)). Finally, soluble and tissue CD44 expression is dramatically upregulated in synovial tissue in rheumatoid arthritis (Haynes et al, Arth. & Rheum. 34:1434 (1991)). These data demonstrate that CD44 synthetic peptides (eg, 3,4,5, 8 or 9), and/or mimetopes of an anti-CD44 antibody Fab binding site (for example, 5F12 (see Example 7 below)), for example, DNA, RNA or peptide mimetopes, can be used as inhibitors of CD44-HA interactions.

CD44 monoclonal antibodies, for example, 5F12, can be used to select ligands, for example, from random RNA, DNA or peptide libraries, that bind to the Fab region of the 5F12 mab with a high affinity and that mimic the HA binding site on CD44H (reviewed in Szostak, TIBS 17:89 (1992) and Tsai et al, J. Immunol. 150:1137 (1993)). As indicated above, such antibody-selected mimetopes (for example, RNA, DNA or synthetic peptide) can be used as inhibitors of HA binding to CD44, and thus as therapeutic agents to inhibit CD44H and CD44E interactions with HA in vivo. More specifically, these mimetopes can be used to treat or prevent tumor cell metastasis of a variety of malignant cell types and to treat inflammatory diseases characterized by upregulation of CD44. Likewise, CD44 monoclonal antibodies, for example, 5F12, can be used in screening protocols to select, from a range of test compounds, those that can be used as inhibitors of the binding of HA to CD44. For example, a test compound can be contacted with a CD44 antibody such as 5F12 and the ability of the antibody to bind the test compound determined. Test compounds for which the antibody has a high affinity can be expected to be useful as inhibitors of CD44-HA binding.

In a further embodiment, the present invention relates to kits comprising container means disposed within which are antibodies to CD44, or peptides thereof, and ancillary agents (buffers, etc.) necessary for determining the metastatic potential of hematopoietic cell types.

The present invention is described in further detail by the following non-limiting Examples.

EXAMPLES

The following protocols and experimental details are referenced in the Examples 1–6 that follow:

Synovial Tissue and Synovial Fluid. Synovial tissue was obtained as discarded tissue from the Duke University Department of Pathology at the time of joint surgery. Synovial fluid was obtained as discarded fluid from the Duke University Clinical Immunology Laboratory at the time of arthrocentesis.

Histopathologic Techniques. Synovial tissues were processed, cut, and studied in indirect immunofluorescence (IF) assays as previously described (Hale et al. (1989) Arth Rhem. 32:22–30). An inflammation score was generated for each synovium using light and IF microscopy based on the degree of T, B, and monocyte infiltration, vessel proliferation, fibroblast and synovial lining cell proliferation as described (Rooney et al. (1988) Arth. Rhem. 31:956–963, McCachren et al. (1990) J. Clin. Immunol. 10:19–27). The degree of reactivity of CD44 and anti-fibronectin antibodies was graded 1+ to 4+ with 1+ signifying reactivity with ≦25% of synovial tissue reactive, 2+>25% and ≦50% of synovial tissue area reactive, 3+>50% and ≦75% of synovial tissue area reactive, and 4+>75% of synovial tissue area reactive.

Monoclonal Antibodies. The following monoclonal antibodies were used: CD44 (A1G3 and A3D8) (Haynes et al. (1983) J. Immunol. 131:1195–1200, Telen et al. (1983) J. Clin. Invest. 71; 1878–1886), anti-fibronectin (FN-15, Sigma, St. Louis, Mo.) 187.1 rat anti-mouse kappa chain (ATCC, Rockville, Md.), 35.1 (CD2) (Martin et al. (1983) J. Immunol. 131:180–185), 9-1 (CD2) (Bernard et al. (1986) Hum. Immunol. 17; 388–405), and P3×63/Ag8 ascites fluid as a negative control.

Flow Cytometry. Flow cytometric analysis was performed on synovial fluid cells using a Becton-Dickinson (Mountain View, Calif.) FACS STAR PLUS flow cytometer in IF assays, as described (Hale et al. (1989) Arth Rhem. 32:22–30, Haynes et al. (1981) New Engl. J. Med. 304:1319–1323).

Characterization of CD44 from Synovial Tissue. Synovial tissue was thawed, homogenized with a Dounce homogenizer in 0.6–1.0 ml extraction buffer (10 mM Tris pH 8.0, 150 mM NaCl, 1% Triton X-100, 20 μg/ml soybean trypsin inhibitor, 1 mM iodoacetamide, and 1 mM PMSF), and centrifuged, (15000 rpm×1 minute). The protein content of supernatants (tissue extracts) was determined using a copper/bicinchoninic acid assay (McCachren et al. (1990) J. Clin. Immunol. 10:19–27) (BCA Protein Assay, Pierce, Rockford, Ill.). Tissue extracts were analyzed by SDS-PAGE on 7% or 10% mini-gels (Mini-Protean II, Biorad Laboratories, Richmond, Calif.), followed by Western blot analysis using alkaline phosphatase-conjugated goat anti-mouse immunoglobulin along with the color development substrates BCIP (5-bromo-4-chloro-3 indolyl phosphate) and NBT (nitro blue tetrazolium) as developing reagents.

Western Blot Analysis of Tissue Extracts. To compare band densities from a given experiment, blots were photographed using TechPan film and resulting positive film densities measured using a laser densitometer. CD44 in trauma synovial tissue was given the value of 1 and the level of CD44 in RA and OA fluids were expressed as a ratio using the equation, $$CD44 \text{ ratio} = \frac{CD44 \text{ in } RA \text{ or } OA \text{ Tissue}}{CD44 \text{ in Trauma Tissue}}.$$

Analysis of Synovial Fluid for CD44 Protein. Synovial fluid specimens were centrifuged, aliquoted, and stored at −80° C. until processed. CD44 protein was immunoprecipitated from aliquots of synovial fluid which were precleared by incubation with P3-Sepharose (control) beads, then precipitated with either A3D8-Sepharose or P3-Sepharose. Immunoprecipitates were removed from the beads by boiling in 0.06M Tris pH 6.8, 10% glycerol, 2% SDS and analyzed by SDS-PAGE and Western blot analysis using alkaline phosphatase conjugated 187.1 rat anti-mouse immunoglobulin. The amount of CD44 in trauma synovial fluid was given the value of 1 and the level of CD44 in RA and OA fluids were expressed as a ratio using the equation, $$CD44 \text{ ratio} = \frac{CD44 \text{ in } RA \text{ or } OA \text{ Fluid}}{CD44 \text{ in Trauma Fuid}}$$

Band densities of CD44 in gels were determined as for tissue above.

Purification of Soluble CD44 Protein. CD44 (A3D8) and control YgGl (P3×63/Ag8) antibodies were conjugated to CNBr-activated Sepharose CL-4B (Pharmacia, Piscataway, N.J.) (3.0 mg IgG/ml gel). HuT 78 T Cell (CD44+) lysate was solubilized from $5 \times 10^9$ cells in 50 ml buffer (300 mM NaCl, 10 mM $Na_2HPO_4$ pH 7.4, 0.2% $NaN_3$w/v 0.5% NP-40 v/v), 0.01% Tween 80 w/v, 0.2 mM phenylmethylsulfonyl fluoride, and 0.1 mM tosyl L-lysine chloromethyl ketone) (0° C.×30 min), centrifuged (4° C. 3000×g×15 min, 23420×g×30 min) filtered, precleared×2 over a P3-Sepharose column, and allowed to bind overnight (4° C.) to A3D8-Sepharose. The column was washed with 5 column volumes equilibration buffer, followed by S column volumes of 50 mM Tris, pH 7.4, 0.5% NP-40. NP-40 was exchanged for octyl glucoside (OG) (Sigma, St. Louis, Mo.) by washing with 2 column volumes 50 mM Tris pH 7.4, 1.5% OG w/v. CD44 protein was eluted with 2.5M $MgCl_2$, 50 mM Tris pH 7.4, 1.5% OG and the column regenerated by washing with 0.1M Tris, 0.5M NaCl, pH 8.5, then 0.1M $NaC_2H_3O_2$, 0.5M NaCl pH 4.5 and finally phosphate buffered saline (PBS). Eluted fractions were dialyzed sequentially against 50 mM Tris pH 7.4+1.5% OG, PBS+1.5% OG, PBS+1.25% OG, and PBS+1% OG using a Centriprep-30 device (Amicon, Danvers, Mass.), and the affinity purification steps repeated until SDS-PAGE silver staining of the resulting CD44 protein preparation revealed only a single band at 80–85 kD that reacted strongly with A3D8 antibody in Western blot analysis.

CD44 Liposomes. Liposomes were prepared by the method of Mimms et al. ((1981) Biochemistry 20:833–840), using 1 μM purified CD44 or control glycophorin protein, 1 nM L-α-dioleoyl lecthin (Avanti Polar Lipids, Birmingham, Ala.), and 240 nM OG. Liposomes were analyzed for content of the appropriate protein using a novel labelling technique and flow cytometry. Liposomes were incubated with 5-(N-octadecanoyl) aminofluorescein (Molecular Probes, Eugene, Oreg.) in PBS×10 min at room temperature. Fluoresceinated liposomes were then reacted with 4.5 mm magnetic beads (Dynabeads M-450 Goat anti-Mouse IgG, Dynal Inc., Great Neck, N.Y.) coated with CD44 (A3D8) or anti-glycophorin (E3,E4,E5) mAbs. After 45 minutes (4° C.), with continuous end-over-end rotation, beads were washed ×3 in PBS using a magnet to immobilize the beads during PBS changes. Fluoresceinated liposome-bead conjugates were then analyzed by flow cytometry.

T Cell Activation Assay. PBMC from healthy donors were stimulated with optimal mitogenic concentration of CD2 mabs 35.1 and 9-1 as described (Denning et al.). Where indicated, CD44 or control glycophorin liposomes (final protein range used was 28–140 nM) were added to these cultures 20 min prior to addition of CD2 mabs. In some experiments PBMC were pretreated with 0.1% bromelain to remove cell membrane CD44 (Telen et al. (1983) J. Clin. Invest. 71:1878–1886, Hale (1989) Immunol. 143:3944–3948).

EXAMPLE 1

Figure 1G:
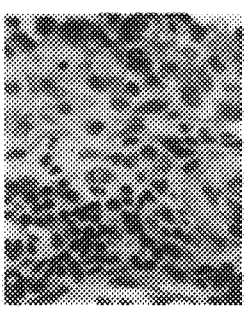
Figure 1H:
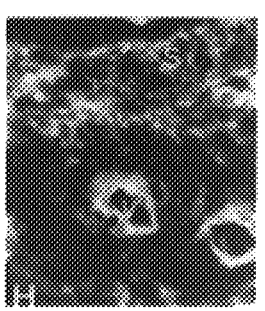
Figure 1I:
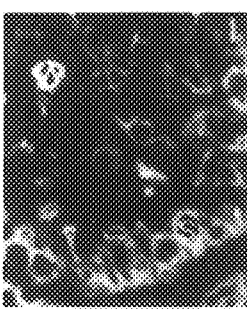
Figure 1J:
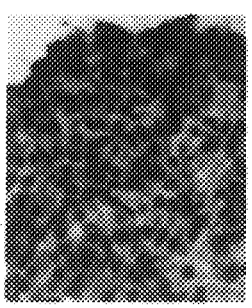
Figure 1K:
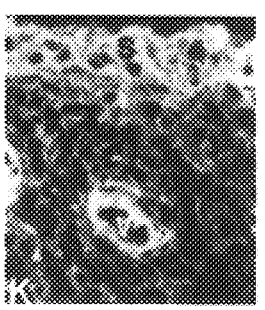
Figure 1L:
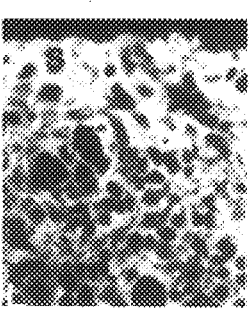

Histologic Analysis of Expression of CD44 and Fibronectin in Trauma Synovium, OA and RA CD44 expression was studied in synovial tissues from 7 RA and 8 OA patients who had surgery for joint replacement and 6 patients who had joint surgery due to joint trauma (Table 3). As a control for CD44, synovial tissue expression was also studied of the extracellular matrix protein, fibronectin. Previous studies have shown fibronectin deposition to be increased in synovial tissues in RA (Scott et al. (1991) Brit. J. Exp. Pathol. 62:362–368). Both CD44 and fibronectin expression were found to be dramatically unregulated in RA synovial tissue compared to their expression in OA or non-inflammed trauma synovium (FIG. 1). In trauma and OA synovium, CD44 and anti-fibronectin mabs reacted with synovial lining cells, vessels and fibroblasts (FIGS. 1A–F). In RA, infiltrating lymphocytes and macrophages, as well as synovial lining cells, vessels and fibroblasts were brightly CD44+ (FIGS. 1G, H, I). In RA with pannus formation, both CD44 and fibronectin were widely expressed throughout synovial tissues (FIGS. 1K, J, L). RA tissues studied had a mean inflammation score of 13.1±2.0 versus 6.6±1.3 in OA tissues. The degree of CD44 mAb reactivity in indirect IF assay was graded (CD44 index, see Methods) on a 1–4 scale with 1 the least CD44 present and 4 the most. The mean CD44 index in RA was 3.6+0.2 versus 1.8±0.2 in OA ($p<0.001$) (Table 4). Thus, CD44 upregulation in synovial tissues in RA was due to two separate mechanisms: 1) increase in expression of CD44 on synovial tissue cell types (synovial lining cells, vessels, fibroblasts), and 2) influx of CD44+ infiltrating immune cells (CD44+ T and B lymphocytes, macrophages).

TABLE 4

Mean Inflammation Score, CD44 Index and Fibronectin Index in RA, OA, and Traumatic Synovium Tissues*

| Disease | Inflammation Score | CD44 Index | Fibronectin Index |
|---|---|---|---|
| Trauma (n = 6) | 9.3 ± 4.2# | 2.0 ± 0.4 | 2.4 ± 0.6 |
| OA (n = 8) | 6.6 ± 1.3 | 1.9 ± 0.2 | 2.3 ± 0.6 |
| RA (n = 7) | 13.1 ± 2.0 | 3.6 ± 0.2** | 3.8 ± 0.1** |

*all values mean ± SEM
**$p < .001$ when compared to trauma or to OA
trauma mean inflammatory index varied from specimen to specimen, range (1–25). No. 229 (inflammation index = 5) was used as a control tissue in biochemical studies.

EXAMPLE 2

Direct Quantitative Assay of the Relative Amount of CD44 Protein in Synovial Tissue The relative amount of CD44 in synovial tissue was determined in 5 OA (nos. 244, 169, 237, 242, and 148), and in 3 RA (nos. 154, 86, and 7) tissues using quantitative Western blot analysis (Table 5). Analysis of the 5 OA synovial tissues demonstrated a mean relative amount of CD44 by Western blot of 3.5±0.7 (ie an average of 3.5×

TABLE 3

Characteristics of Patients From Whom Synovial Tissue Was Obtained For Study

| Patient | Age | Disease | Medications at Duration | Tissue Surgery | Site | Inflam. Score | CD44 Index | Fibro. Index |
|---|---|---|---|---|---|---|---|---|
| RA | | | | | | | | |
| 154 | 68 | RA | 8 yrs | Pred | Knee | 21 | 4+ | 4+ |
| 146 | 60 | RA | >20 yrs | Pred, Mtx | Knee | 13 | 4+ | 4+ |
| 90 | 61 | RA | 5 yrs | NSAID, Mtx | PIP | 14 | 3+ | 3+ |
| 86 | 72 | RA | >10 yrs | NSAID, ASA | Knee | 18 | 3+ | 4+ |
| 38 | 68 | RA | 16 yrs | NSAID, ASA | Knee | 8 | 4+ | 4+ |
| 7 | 62 | RA | 10 yrs | ASA, Pred, NSAID, Au | PIP | 13 | 4+ | 4+ |
| 127 | 59 | RA | 15 yrs | Pred, TLI | Shoulder | 5 | 3+ | 4+ |
| OA | | | | | | | | |
| 20 | 58 | OA | 10 yrs | ASA, IAS | Knee | 8 | 2+ | 4+ |
| 11 | 71 | OA | 10 yrs | ASA | Knee | 8 | 2+ | 3+ |
| 36 | 60 | OA | 5 yrs | None | Hip | 5 | 1+ | 1+ |
| 198 | 60 | OA | 2 yrs | NSAID | Hip | 3 | 2+ | 2+ |
| 242 | 78 | OA | 8 yrs | NSAID | Knee | 14 | 3+ | 4+ |
| 244 | 71 | OA | 13 yrs | NSAID | Knee | 4 | 2+ | 2+ |
| 169 | 81 | OA | 7 mo. | NSAID | Shoulder | 8 | 1+ | 2+ |
| 237 | 74 | OA | 20 yrs | NSAID | Knee | 3 | 1+ | 1+ |
| Trauma | | | | | | | | |
| 148 | 72 | Trauma | 4 mo. | NSAID | Shoulder | 5 | 1+ | 1+ |
| 212 | 42 | Trauma | 1 yr | NSAID | Elbow | 25 | 3+ | 4+ |
| 211 | 22 | Trauma | 6 mo. | None | MTP | 10 | 3+ | 4+ |
| 229 | 35 | Trauma | 1 yr | ASA | Toe | 5 | 1+ | 2+ |
| 161 | 36 | Traum | 19 yrs | None | PIP | 1 | 1+ | 1+ |
| 250 | 52 | Trauma | 9 mo. | None | MCP | 4 | 1+ | 1+ |

Figure 2A:
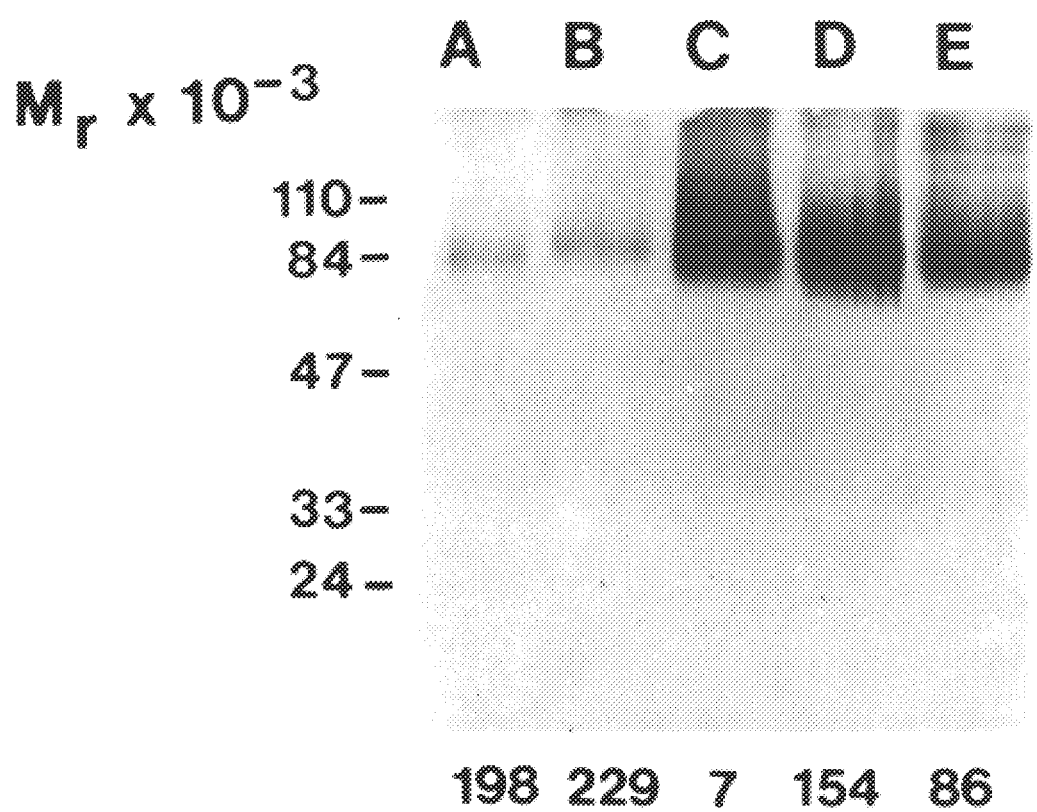
FIGS. 2A and 2B. Quantitative Western Blot Analysis of CD44 Protein in Synovial Tissue. Equal amounts of tissue were extracted from each synovium and run on SDS-PAGE followed by Western blot analysis with anti-CD44 mab A3D8.
Figure 2B:
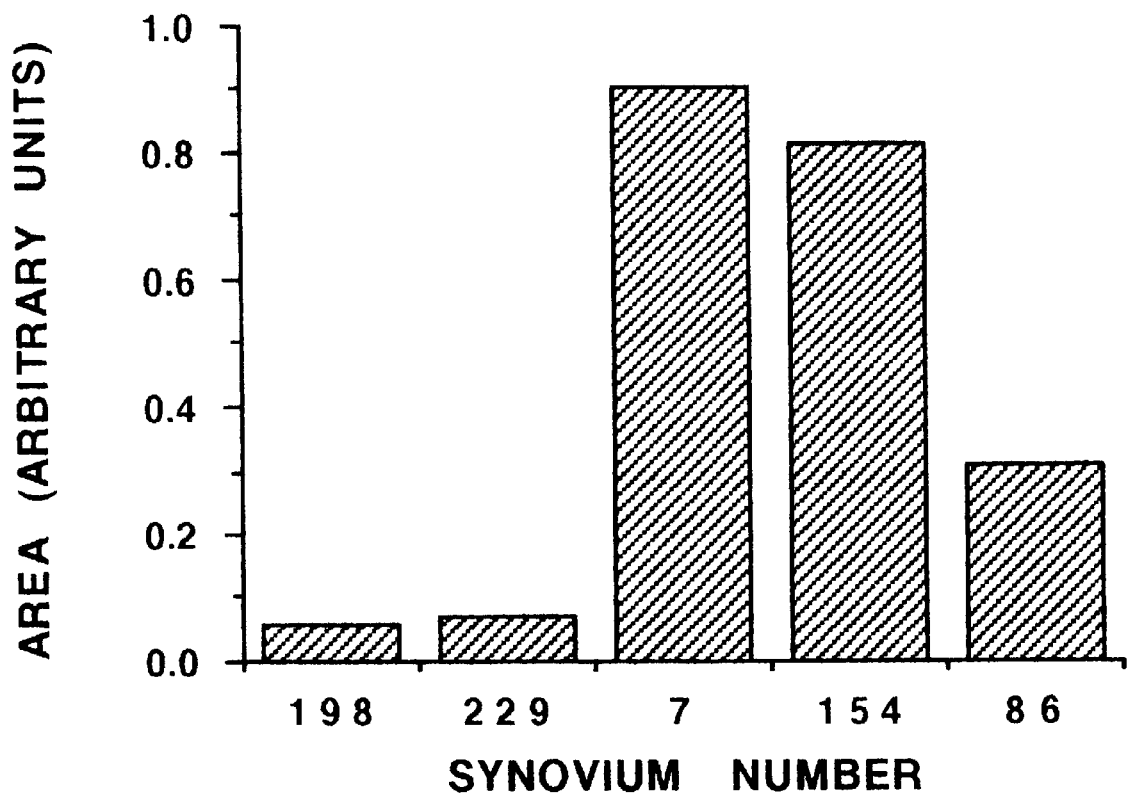

Pred, prednisone
Mtx, methotrexate
NSAID, non-steroidal anti-inflammatory agent
ASA, aspirin
Au, gold therapy
TLI, total lymphoid
IAS, intraarticular steroids
The diagnosis of RA was made using ACR criteria.

more CD44 than in trauma synovial tissue no. 229). In contrast, RA synovial tissues contained a mean relative amount of CD44 by Western blot of 10.7±1.7 (Table 5). A representative Western blot of CD44 levels in trauma synovium (no. 229), RA synovium (nos. 7,154, and 86) and in a representative OA synovium (no. 198) is shown in FIG. 2A. FIG. 2B shows the relative amounts of CD44 in each synovial tissue as determined by the actual value obtained by laser densitometry of the same Western blot gel. Thus, quantitative Western blot analysis demonstrated RA tissue contained 3 fold more CD44 per gram of wet tissue than did OA tissue, 11 fold more than trauma synovium, and demonstrated that the amount of synovial tissue CD44 correlated with the degree of inflammation present (Table 5).

TABLE 5

Mean Relative CD44 Protein Levels in OA and RA Synovial Tissues Determined by Western Blot Analysis

| Disease | Inflammation Score | CD44 Index* | CD44 Protein Level# |
|---|---|---|---|
| OA (n = 5) | 6.4 ± 2.1 | 2.0 ± 0.3 | 3.5 ± 0.7 |
| RA (n = 3) | 17.3 ± 2.3 | 4.0 ± 0@ | 10.7 ± 1.7** |

*CD44 index determined by histologic IF analysis.
CD44 protein level determined by quantitative Western blot analysis. Data are arbitrary units relative to CD44 levels found in trauma synovium no. 229 (relative CD44 level = 1, inflammatory index = 5).
@ $p < .01$ when compared to OA.
**$p < .005$ when compared to OA.

EXAMPLE 3

Figure 3:
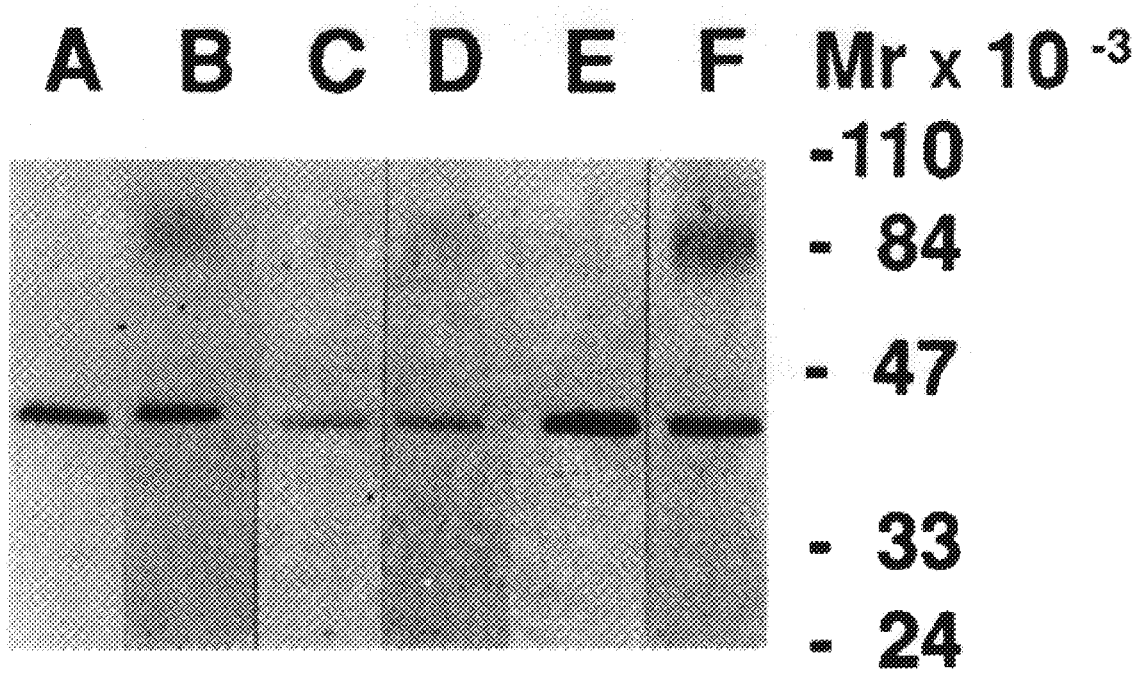
FIG. 3. Western Blot Analysis of CD44 Protein in Trauma, OA and RA Synovial Fluid. Lanes A, C, and E are control lanes in which CD44 protein was immunoprecipitated with CD44 mab and then run in Western blot analysis and blotted with control P3X63/Ag8 IgG1 paraprotein. Lanes B, D, and F are CD44 protein immunoprecipitated with CD44 mab and then blotted with CD44 mab. Lanes A and B are from synovial fluid no. 11 (trauma, cell count 450, relative CD44 level=1.0) lanes C and D are from synovial fluid no. 29 (OA, cell count 3,469, CD44 level=0.77) and lanes E and F from RA synovial fluid 13 (cell count 11,061, CD44 level 1.69).
Figure 4:
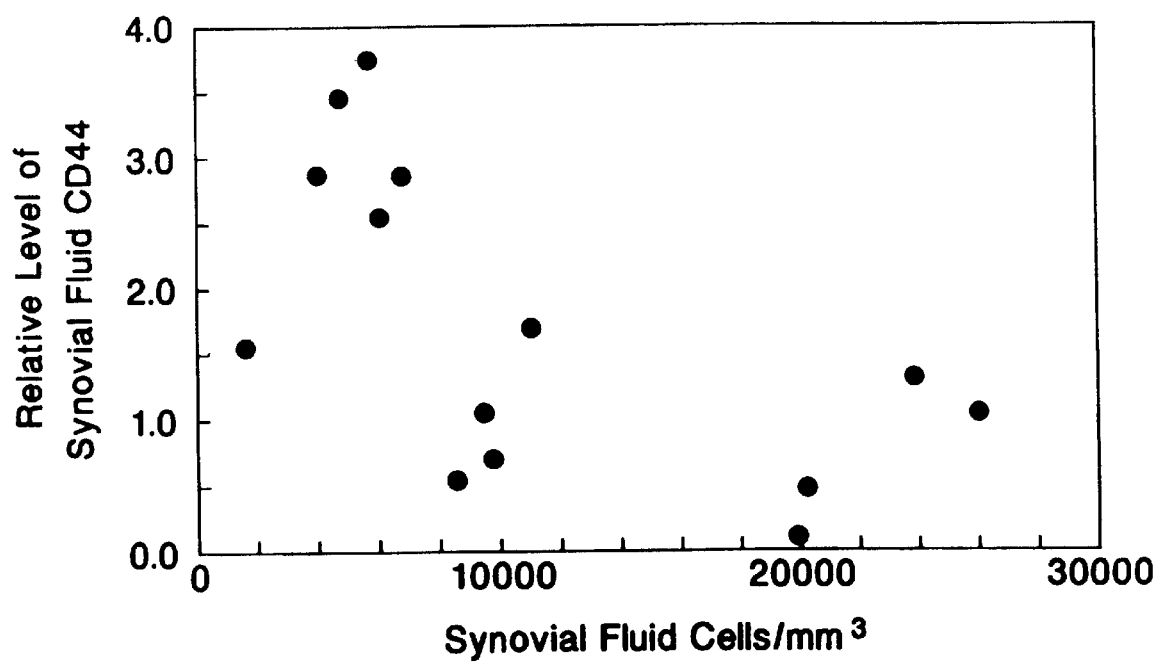
FIG. 4. Comparison of RA Synovial Fluid Cell Counts Versus Relative Levels of Synovial Fluid CD44 Protein.
Figure 6:
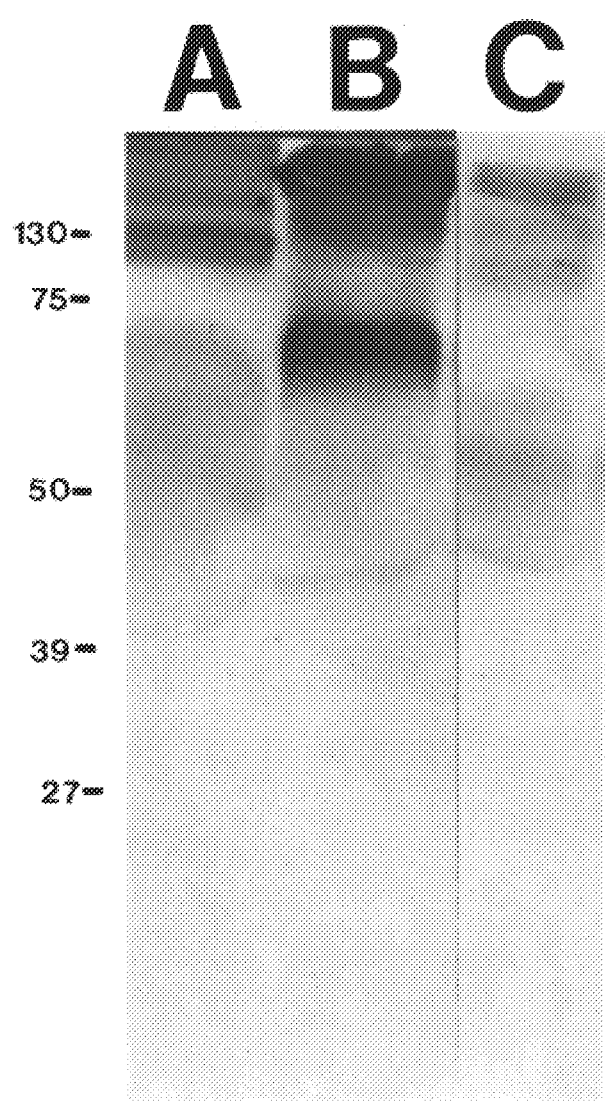
FIG. 6. Shows a western blot analysis of recombinantly produced CD44-Rg-2 protein that could be used as an immunosuppressive agent to inhibit CD44-mediated proinflammatory functions.
Figure 7:
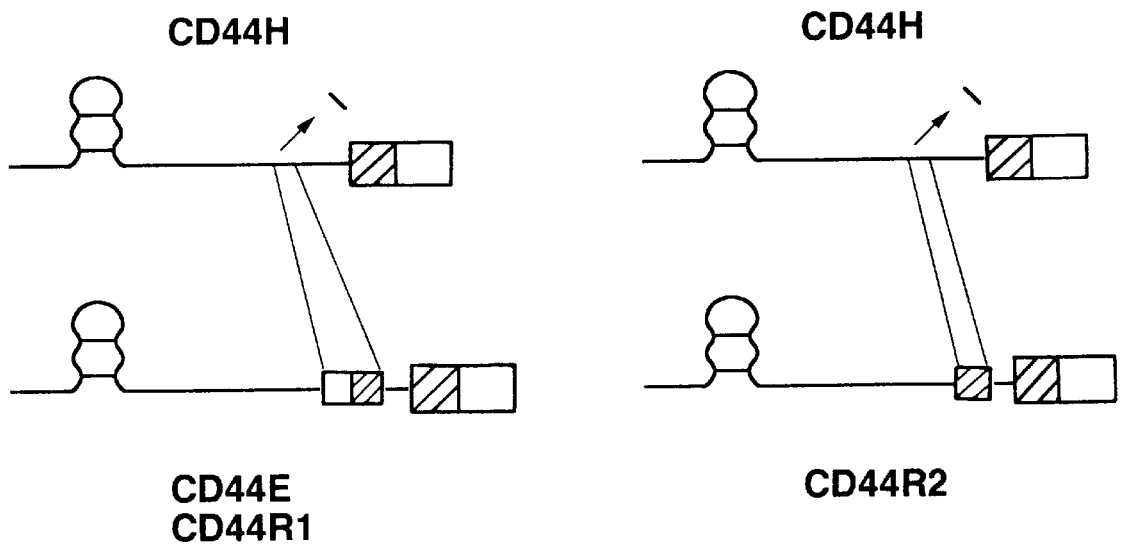
FIG. 7. Schematic representation of formation of splice variants of CD44 resulting in deletion of a small segment of CD44H (ATR). C-terminal open box is the CD44 cytoplasmic domain. Shaded C-terminal box is the CD44 transmembrane region. Solid and open boxes represent the portions of domains 4 and 5 of CD44 that are in CD44 forms CD44E (R1) and CD44R2.
Figure 8:
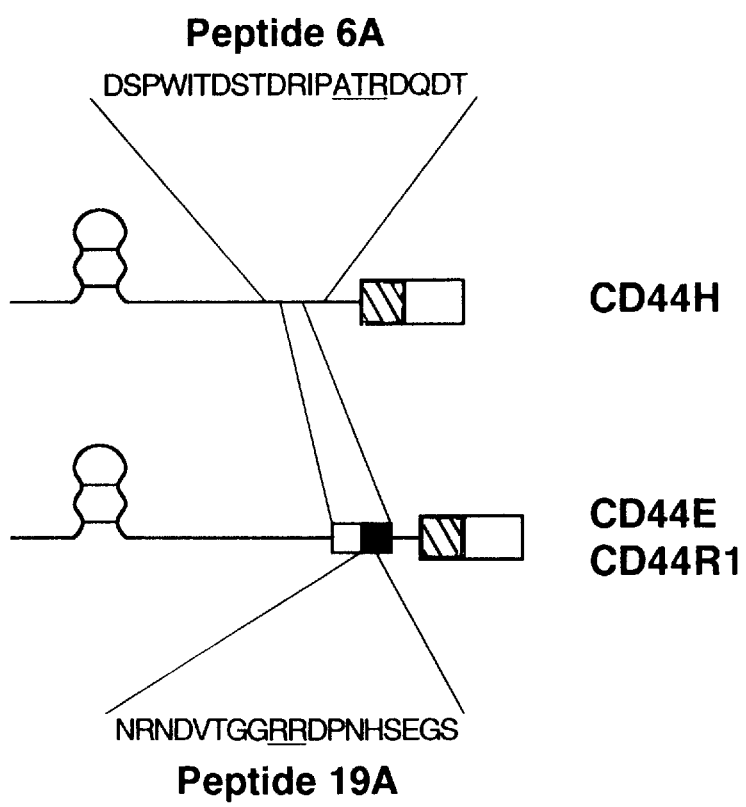
FIG. 8. Sequences of CD44-6A (SEQ ID NO:7) and CD44-19A (SEQ ID NO:18) peptides relative to the intact CD44E(Rl) and CD44H molecules. The CD44-6A peptide contains an ala-thr-arg (ATR) sequence that is deleted in the process of splicing in the various inserts to form CD44 splice variants. The CD44-19A peptide is amino acids 287–304 of the insert of domains 4 and 5 that is present in the CD44E (R1) form.
Figure 9A:
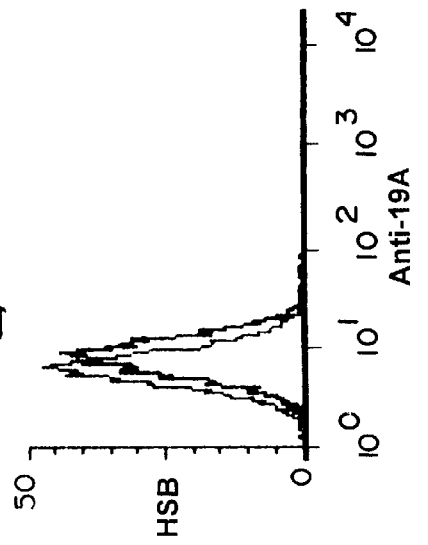
FIGS. 9A–F. Flow cytometric analysis of reactivity of the anti-CD44 mab A3D8 and antisera against peptides 6A and 19A with HSB and HT29 cells. The anti-CD44 mab, A3D8, reacted with cells expressing CD44H FIG. 9(A) and CD44E FIG. 9(B), while the anti-6A serum reacted only with the cells expressing CD44H FIG. 9(C) but not cells expressing CD44E FIG. 9(D), in contrast, the anti-19A serum reacted with only with cells expressing the CD44E FIG. 9(F) but not with cells expressing CD44H FIG. 9(E). Pre-immune sera or P3 mab were used as controls (labelled leftmost plot) and post-immune sera or A3D8 is rightmost plot.
Figure 9C:
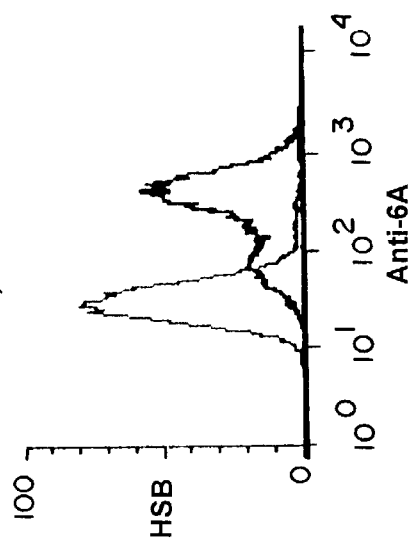
Figure 9E:
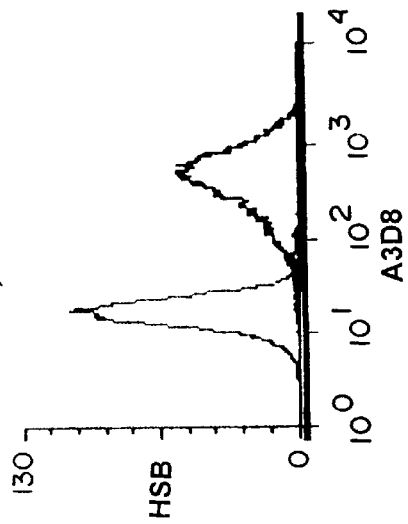
Figure 9B:
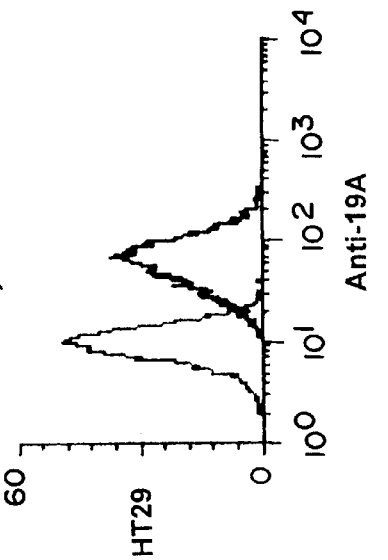
Figure 9D:
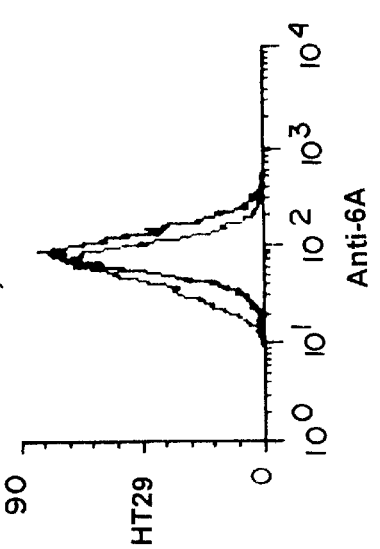
Figure 9F:
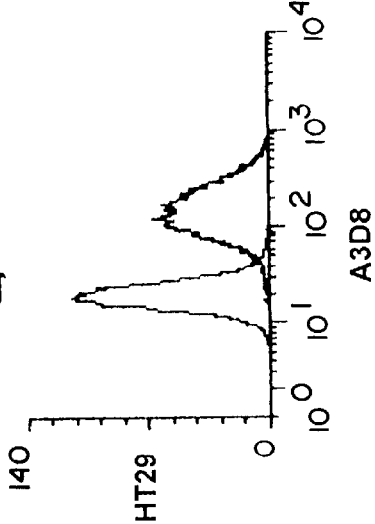
Figure 10A:
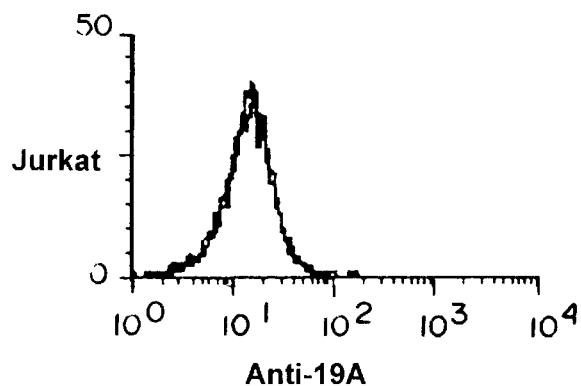
FIGS. 10A–F. Specificity of anti-6A and anti-19A sera with CD44H and CD44E Jurkat transfectants examined by flow cytometry Anti-19A serum was tested on Jurkat cells FIG. 10(A), CD44H FIG. 10(B) and CD44E FIG. 10(C) Jurkat transfectants. Anti-6A serum was tested on Jurkat cells FIG. 10(D), CD44H FIG. 10(E) and CD44E FIG. 10(F) transfectants (pre-immune sera were used as controls and leftmost plot and post-immune sera or A3D8 is rightmost plot).
Figure 10D:
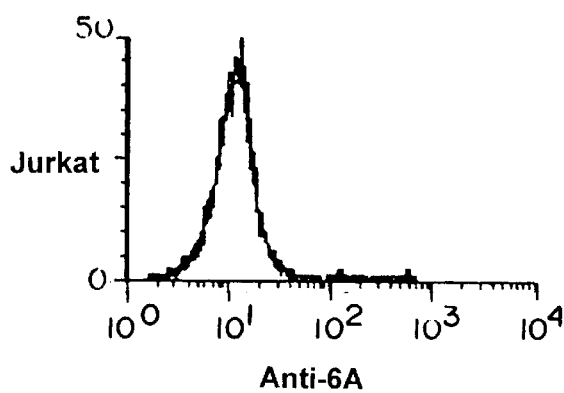
Figure 10B:
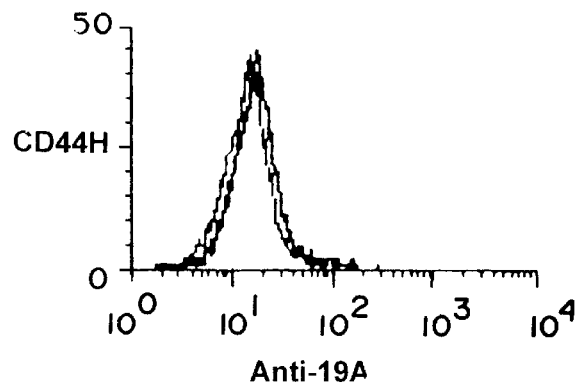
Figure 10E:
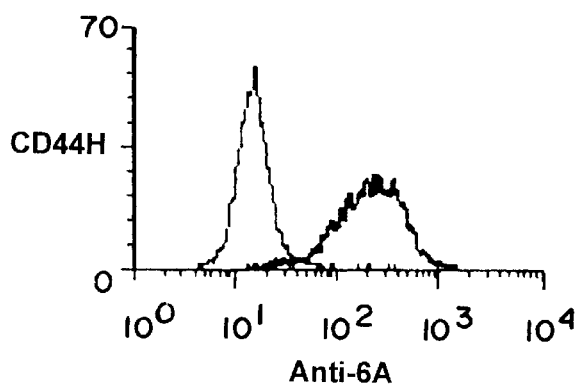
Figure 10C:
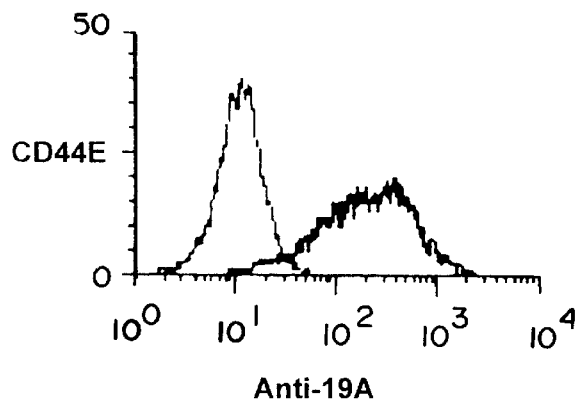
Figure 10F:
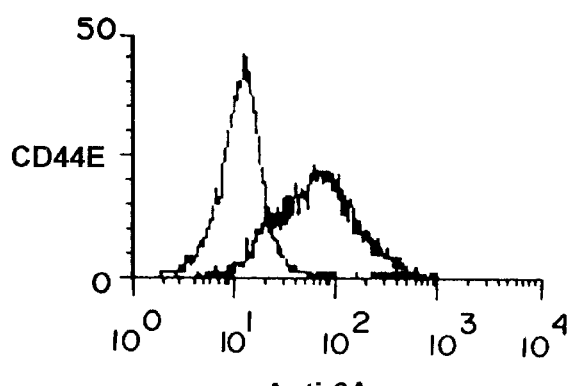

Comparison of the Relative Levels of Soluble CD44 in RA Versus OA Synovial Fluid Because CD44 protein has been shown to circulate in a soluble form in plasma and serum (Telen et al. (1983) J. Clin. Invest. 71:1878–1886), a determination was made whether the soluble CD44 was present in trauma, RA and OA synovial fluid. For this analysis, immunoprecipitation of CD44 antigen from 200 μl of synovial fluid followed by quantitative Western blot analysis was used. In 5 OA synovial fluids studied, the mean WBC was 1250±577 cells/$mm^3$ and the mean level of CD44 was 0.94±2 [ie, was 0.94× the level of CD44 found in trauma synovial fluid no. 11]. In RA synovial fluid, the mean cell count was elevated (11, 279±2107) ($p<0.025$ compared to OA) and the mean CD44 level was near double that of trauma and OA synovial fluid (1.91±0.4) ($p<0.001$) (Table 6). FIG. 3 shows examples of CD44 in RA versus OA and trauma synovial fluids. Thus, RA synovial fluid contained an average of 2 fold more soluble CD44 than OA or trauma synovial fluid, and the mean RA synovial cell count was higher than for OA (Table 6). However, when individual RA synovial fluid cell counts were plotted versus the relative level of RA synovial fluid CD44, a significant trend was observed to be present such that higher CD44 levels occurred in synovial fluid samples with lower cell counts (Spearman Rank order correlation, r=−0.68, $p<0.01$) (FIG. 6). When RA synovial fluids were grouped according to cell count, RA synovial fluids with low cell counts (<7000 cells/$mn^3$) had 3.3× (2.84±0.3 mean ±SEM relative CD44 level) more CD44 than did RA synovial fluids with higher cell counts (>8500 cells/$mm^3$) (0.85+0.35 mean±SEM relative CD44 level). Thus, higher levels of soluble CD44 were present in RA synovial fluids with lower cell counts, and synovial fluid CD44 decreased to sub-normal levels in the more inflammatory RA synovial fluids.

TABLE 6

Quantitation of CD44 Levels in OA and RA Synovial Fluid

| Patient | Diagnosis | Cell Count ($mm^3$) | CD44 Protein Level* |
|---|---|---|---|
| 18 | RA | 1,634 | 1.55 |
| 31 | RA | 4,047 | 2.87 |
| 25 | RA | 4,776 | 3.45 |
| 6 | RA | NA | 4.81 |
| 26 | RA | 5,737 | 3.74 |
| 22 | RA | 6,080 | 2.55 |
| 30 | RA | 6,820 | 2.87 |
| 15 | RA | 8,565 | 0.54 |
| 23 | RA | 9,472 | 1.05 |
| 33 | RA | 9,772 | 0.70 |
| 13 | RA | 11,061 | 1.69 |
| 17 | RA | 19,840 | 0.00 |
| 12 | RA | 20,214 | 0.47 |
| 35 | RA | 23,867 | 1.31 |
| 34 | RA | 26,024 | 1.04 |
| mean ± SEM | | 11,279 ± ,107 | 1.91 ± 0.36 |
| 5 | OA | 98 | 1.38 |
| 16 | OA | 798 | 1.24 |
| 24 | OA | 831 | 0.57 |
| 10 | OA | 1,072 | 0.73 |
| 29 | OA | 3,469 | 0.77 |
| mean ± SEM | | 1,250 ± 477 | 0.94 ± 0.16 |

*Data are arbitrary units relative to CD44 level found in trauma synovial fluid no. 11 (cell count 450, relative CD44 protein level taken as 1.0). The types of medications taken by RA patients with WBC >8500 did not differ from medications taken by RA patients with WBC <7000. RA Patient 17 also had calcium pyrophosphate crystals present in join fluid.

EXAMPLE 4

Figure 5A:
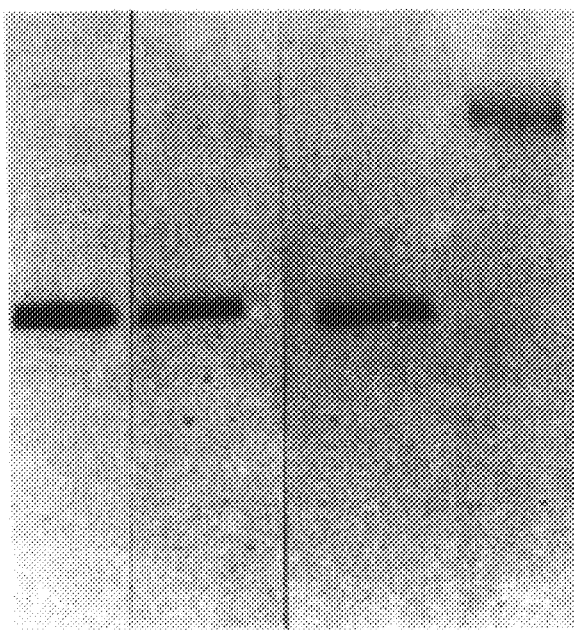
FIGS. 5A and 5B. Western Blot Analysis of CD44 Protein in Synovial Fluid from non-RA Types of Inflammatory Synovitis.
Figure 5B:
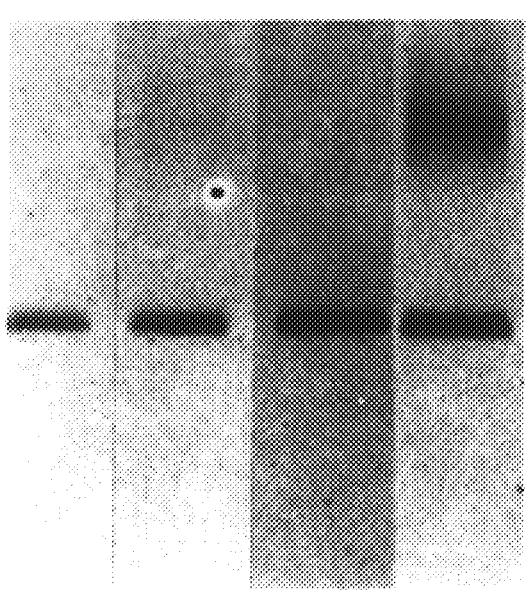

Effect of Elevated Synovial Fluid Cell Counts on Soluble CD44 Levels in Non-RA Forms of Inflammatory Synovitis To determine if elevated synovial fluid cell counts of >8500/$mm^3$ were associated with normal or depressed synovial fluid CD44 levels in diseases other than RA, 3 non-RA inflammatory synovial fluids were studied, no.14 (*Staphylococus aureus* septic arthritis, cell count, 371,915/$mm^3$), no. 32 (gout, cell count, 35,400/$mm^3$), and no.100 (psoriatic arthritis, cell count, 9294/$mm^3$). CD44 levels were elevated in all three cases above the mean CD44 found level in high-cell-count RA fluid (no. 14, CD44 level=2.45; no. 32, CD44 level=3.79; no. 100, CD44 level=7.00) (FIGS. 5A, 5B). Thus, decrease of RA synovial fluid CD44 levels in the presence of higher (>8500/$mm^3$) cell count was not a general phenomenon related solely to the number of synovial inflammatory cells present.

EXAMPLE 5

Effect of Soluble CD44 Protein on T Cell Activation

Because soluble CD44 antigen levels decreased in RA synovial fluids with high cell counts but not in gout or in other non-RA inflammatory synovial fluids, and because cell-associated CD44 is involved in T cell activation (Denning et al., Huet et al. (1989) Immunol. 798–801, Shimuzu et al. (1989) J. Immunol. 143:2457–2463), potential immunologic sequelae of decreased levels of soluble CD44 in inflammatory RA synovial fluids on T cell function were determined. To directly assess the effect of soluble CD44 protein on T cell activation, CD44 was affinity-purified from T cell membranes, incorporated into liposomes, and incubated with peripheral blood mononuclear cells (PBMC) prior to stimulation with CD2 antibodies (a potent stimulus of T cell activation) (Denning et al., Stamenkovic et al. (1989) Cell 56:1057–1062). Initial experiments showed that CD44 protein-containing liposomes alone had no effect on the proliferation of T cells (data not shown). However, when CD44 protein-containing liposomes (CD44 concentration 140 nM) were added to PBMC prior to addition of CD2 antibodies, T cell proliferation was significantly decreased by 35±4% (n=4, p<0.02) (Table 7) as compared to addition of control (glycophorin-containing) liposomes. The cysteine protease, bromelain, was previously shown to remove surface CD44 from T cells (Telen et al., Hale et al. (1989) Immunol. 143:3944–3948). As a control, no suppression of T cell activation was observed when CD44 protein-containing liposomes were added to bromelain-treated PBMC (average suppression 0.5±7%, n=3, p=NS) (Table 7).

TABLE 7

Effect of Soluble CD44 Protein on CD2-Mediated T Cell Activation*

| Treatment | Additions to Culture | cpm/$10^6$ Cells |
|---|---|---|
| Sham treated PBMC | Media | 460 |
| | CD2 mAb | 308,230 |
| | CD2 mAb + CD44 liposomes | 172,960 |
| | CD2 mAb + control liposomes | 255,090 |
| Bromelain-treated PBMC | Media | 5,380 |
| | CD2 mAb | 552,440 |
| | CD2 mAb + CD44 liposomes | 646,830 |
| | CD2 mAb + control lipsomes | 550,000 |

*Data shown is from a single experiment representative of 4 experiments with sham-treated cells and 3 matched experiments with bromelain-treated cells. Protein concentration for both CD44 and glycophorin liposomes added in this experiment was 140 nM. The mean suppression of CD2 proliferation by sham-treated PBMC in the presence of CD44 liposomes in 4 separate experiments was 35 ± 4% (mean ± SEM) as compared to control lipsomes (p <0.02, paired t-test). Addition of CD44 lipsomes to bromelain treated PBMC had no significant effect on CD2-mediated proliferation (mean increase 5 ± 7%, p = NS) as compared with control liposomes. Identical results were obtained when soluble, free CD44 protein was added to CD2 stimulated PBMC culture (Data not shown).

EXAMPLE 6

Reactivity of Anti-CD44-6A and Anti-CD44-19A Antibodies

Anti-sera raised against CD44 synthetic peptides (anti-CD446A and anti-CD4419A) when injected into rabbits, gave rise to polyclonal antisera that reacted with CD44+cells (FIG. 9), and reacted with Jurkat T cell ALL cells that were transfected with either CD44H (in the case of anti-6A serum) or CD44E (in the case of anti-19A serum) (FIG. 10).

The CD44-6A and the CD44-19A peptides can inhibit T cell activation and antisera against these peptides can also inhibit T cell activation. Table 8 shows that addition of 1 mg/ml of either CD44-6A or CD44-19A peptide to anti-CD3 monoclonal antibodies triggered peripheral blood mononuclear cell in vitro cultures and resulted in inhibition of T cell activation. Table 9 demonstrates that the rabbit polyclonal antisera against either the 6A or the 19A peptides also inhibited the in vitro T cell proliferative response to anti-CD3 is monoclonal antibodies.

TABLE 8

INHIBITION OF T CELL RECEPTOR-MEDIATED T CELL ACTIVATION BY CD44 PEPTIDES

| Additions To In Vitro Cultures of Peripheral Blood Mononuclear Cells | Δ CPM 3H-Thymidine/106 Cells in Culture (% Inhibition) |
|---|---|
| Media + Anti-CD3ϵ mab Leu 4 (1:10,000) | 170,523 |
| CD446A Peptide (1 mg/ml) + Anti-CD3ϵ mab Leu 4 (1:10,000) | 56,858 (67%) |
| Media Anti-CD3ϵ mab Leu 4 (1:1000) | 199,816 |
| CD4419A Peptide (1 mg/ml) + Anti-CD3ϵ mab Leu 4 (1:1000) | 50,318 (75%) |

Synthetic peptides were prepared by F-Moc or T-Boc chemistry, purified using HPLC, and resuspended in RPMI media prior to addition to 4 day in vitro cultures. Following 4 days in culture, 3H-thymidine was added, and following an incubation of 4 hours, the cultures were harvested using an automated multiwell harvester using standard techiques.

TABLE 9

INHIBITION OF T CELL RECEPTOR-MEDIATED T CELL ACTIVATION BY SERA AGAINST CD44 PEPTIDES

| Additions To In Vitro Cultures of Peripheral Blood Mononuclear Cells* | Δ CPM 3H-Thymidine/106 Cells in Culture (% Inhibition) |
|---|---|
| Control Prebleed Serum (1:500) + Anti-CD3ϵ mab OKT3 (1:1,000) | 102,460 |
| Anti-CD446A Peptide Serum (1:500) + Anti-CD3ϵ mab OKT3 (1:1,000) | 52,305 (49%) |
| Control Prebleed Serum + Anti-CD3ϵ mab OKT3 (1:1000) | 131,009 |
| Anti-CD4419A Peptide Serum (1:200) + Anti-CD3ϵ mab OKT3 (1:1000) | 67,510 (49%) |

*All sera were raised in rabbits by conjugation of the synthetic peptide to tetanus toxoid (Wyeth-Ayerst Laboratories, Marietta, GA). The 19A CD44 peptide was conjugated to tetanus toxoid according to the method of Greene et al., (1982) Cell 28:477–487. The 6A CD44 peptide was conjugated to tetanus toxoid according to the method of Avrameas, (1969) Immunochemistry 6:43–52. The conjugated peptide was injected subcutaneously in multiple sites, in rabbits, initially in complete Freund's adjuvant, and boosted in incomplete Freund's adjuvant as described in Ware et al., J. Immunol. (1989) 143:3632–3640.

EXAMPLE 7

Modulation of Hyaluronan (HA) Binding to CD44 by CD44 Antibodies

Experimental Approach:
Mabs:

Human CD44 mab 5F12, AlG3 and A3D8 have been described previously (Liao et al, J. Immunol. in press (1993)). 5F12 IgG was purified from serum-free supernatant of 5F12 hybridoma cell line by Affi-gel Protein A MAPS II column (Bio-Rad, Richmond, Calif.). 5F12 Fab$_2$ and Fab fragments were prepared by digestion of 5F12 whole IgG with pepsin or papain, and purified by protein A column. Fluorocein isothocyanate (FITC) labeled 5F12 IgG was prepared as described previously (Aruffo et al, Cell 61:1303 (1990)) and used for determination of cross-reactivity of other CD44 mabs. P3×63 paraprotein (P3) IgG was purified from serum-free supernatant of the P3×63Ag8.652 myeloma cell line, and used as a negative control in mab binding assays.

Cell cultures:

CD44H transfected Jurkat T cell lines have been previously described (Liao et al, J. Immunol. Dec. 1, 1993). Cells were treated with 10 ng/ml PMA overnight and used in mab and HA binding assays as described (Liao et al, J. Immunol. Dec. 1, 1993). cos African Green Monkey cells were cultured in DMEM (GIBCO, Life Technologies, Grand Island, N.Y.) supplemented with FCS 10% (v/v), and baboon lymphoblast cell line 26 CB-1 were cultured in RPMI 1640 medium (GIBCO, Life Technologies, Grand Island, N.Y.) supplemented with FCS 10% (v/v).

Immunofluorescence analysis and HA binding Assay:

Ability of CD44 mabs to block the binding HA to CD44H transfected Jurkat T cells, and cross reactivity of CD44 mabs were analyzed by flow cytometry and indirect immunofluorescence as described (Liao et al, J. Immunol. Dec. 1, 1993). All incubations and washes were carried at 4° C. For analysis of surface expression of CD44 on cos cells, subconfluent cell culture was washed once with PBS, incubated with 0.02% EDTA for 5 min at 37° C. to disperse cells. Cells were harvested in PBS with 2% BSA.

Preparation of Soluble CD44-Immunoglobulin (Rg) Fusion Protein:

CD44-Rg expression plasmid produces hybrid CD44-Rg molecules comprised of the full extracellular domain of CD44H and the human IgG hinge, CH2 and CH3 regions of $IgG_1$ heavy chain (gift from Brian Seed, Boston, Mass.) (Miyake et al, J. Exp. Med. 172:69 (1990)). CD44-Rg plasmid was transfected into cos cells and the CD44-Rg fusion protein was prepared from the supernatants of the transfected cos cells and purified by Protein A chromatography as described (Miyake et al, J. Exp. Med. 172:69 (1990)). The $NH_2$-terminal amino acid sequence of CD44-Rg was determined by automated amino acid sequencing (Applied Biosystems, Inc. Model 470A). SDS-PAGE and Western blotting:

SDS-PAGE and Western blot analysis of reactivity of CD44 mabs with CD44 protein or CD44-Rg was performed as described (Liao et al, J. Immunol. Dec. 1, 1993). CD44H transfected Jurkat T cells were washed twice with ice-cold PBS and lysed in 10 mM Tris-Cl, pH 7.4, 0.5% NP40, 150 mM NaCl, 25 mM EDTA, 10 μg/ml aprotinin, 1 mM phenylmethysulfonyl fluoride, and 20 mM iodacetemide). Cell lysates (approximately $1×10^6$ cells/lane) and the purified CD44-Rg (100 ng/lane) were resolved by 7.5% SDS-PAGE under non-reducing conditions. The resulting gel was electrophoretically blotted onto a nitrocellulose filter. The filter was blocked in 10% non-fat milk, reacted with CD44 mabs or control mab and then incubated with goat anti-mouse IgG-alkline phosphotase conjugate (Promega, Madison, Wis.) and followed by incubation with substrate for visualization.

cDNA cloning and sequencing of African Green Monkey CD44:

Total cellular RNA was isolated from Cos cells by guanidium isothiocyanate lysis and centrifugation through cesium chloride. Total cellular RNA (5 μg) was transcribed using reverse transcriptase (Pharmacia LKB Biotechnology) with a down stream primer (GGATCTAGATTACACCCCAATCTTC) (SEQ ID NO:21) complementary to the 3' sequence of human CD44, and then amplified for 25 cycles by PCR using Pfu (Stratagene, LaJolla, Calif.) and a up-stream primer (5' GCCAAGCTTCCACCATGGACAAGTTTTGG 3') (SEQ ID NO:22), which is complementary to the negative strand of human CD44 cDNA. Oligonucleotides were designed to place unique HindIII and XbaI sites to flank the 5' and 3' ends of CD44 cDNA. Resulting African Green Monkey CD44 cDNA were digested with restriction enzymes HindIII and XbaI and then inserted between the HindIII and XbaI sites of plasmid vector CDM8 (Miyake et al, J. Exp. Med. 172:69 (1990)). The sequence of African Green monkey cos cell CD44 cDNA was obtained by dideoxynucleotide sequencing technique using sequenase (US Biochemicals, Cleveland, Ohio).

Figure 11:
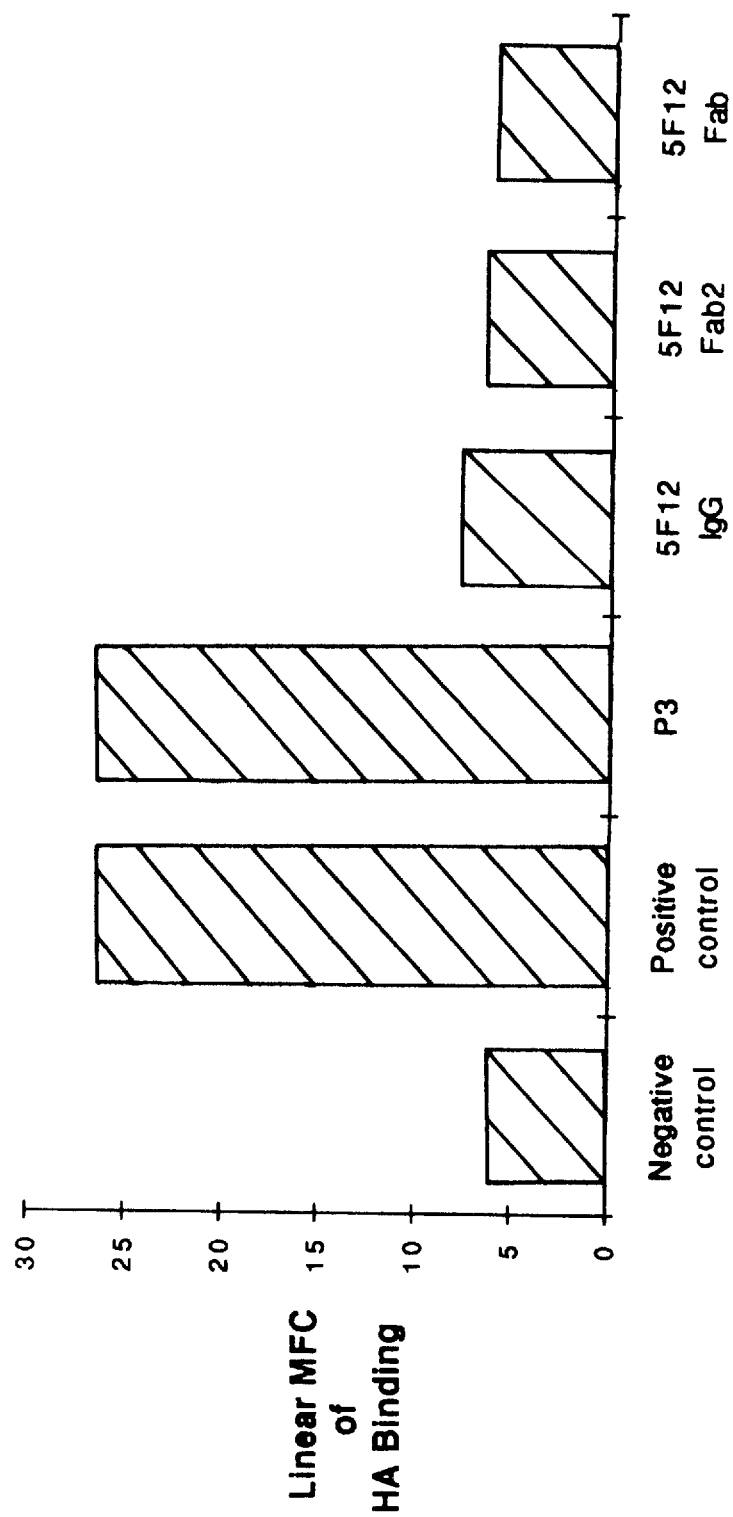
FIG. 11. Effects of CD44 mab 5F12 on the binding of HA to CD44H transfected T cells. Cells ($1 \times 10^6$) were incubated with 1.25 μg of the purified whole 5F12 IgG. $Fab_2$ or Fab mab fragments for 30 min at 4° C. followed by incubation of HA-FITC. Results were expressed as linear MFC analyzed by flow cytometry, and are representative of three separate experiments.

Results:

Inhibition of HA-FITC binding to CD44-transfectant Jurkat T cells by CD44 monoclonal antibody 5F12:

Monoclonal antibodies A1G3 and A3D8 did not inhibit the binding of HA to CD44, but rather augmented the binding of HA-FITC to CD44H transfectant Jurkat cells (Liao et al, J. Immunol. in press (1993)) (Table 10). In contrast, monoclonal antibody 5F12 blocked HA-FITC binding to CD44H-transfectant Jurkat T cells completely (Table 10). FIG. 11 demonstrates that purified IgG of monoclonal antibody 5F12, $Fab_2$ fragments of 5F12, and Fab fragments of 5F12 all blocked HA-FITC binding to CD44H-transfected Jurkat T cells.

TABLE 10

Inhibition of HA-FITC Binding to CD44 Transfected Jurkat T Cells by CD44 Mabs

| Name of mabs | HA-FITC Binding | |
|---|---|---|
| | MFC | % Change |
| P3 | 24 | 0 |
| A3D8 | 30 | +13 |
| A1G3 | 34 | +50 |
| 5F12 | 4 | −100 |

$$\% \text{ Inhibition} = \left(1 - \frac{\text{Linear MFC of HA-FITC Binding with Mab} - \text{Negative}}{\text{Linear MFC of Positive Control} - \text{Negative}}\right)$$

MFC of positive control (cells strained with HA-FITC without addition of antibody) = 24, and MFC of negative control (unstained cells) = 4.

Figure 12:
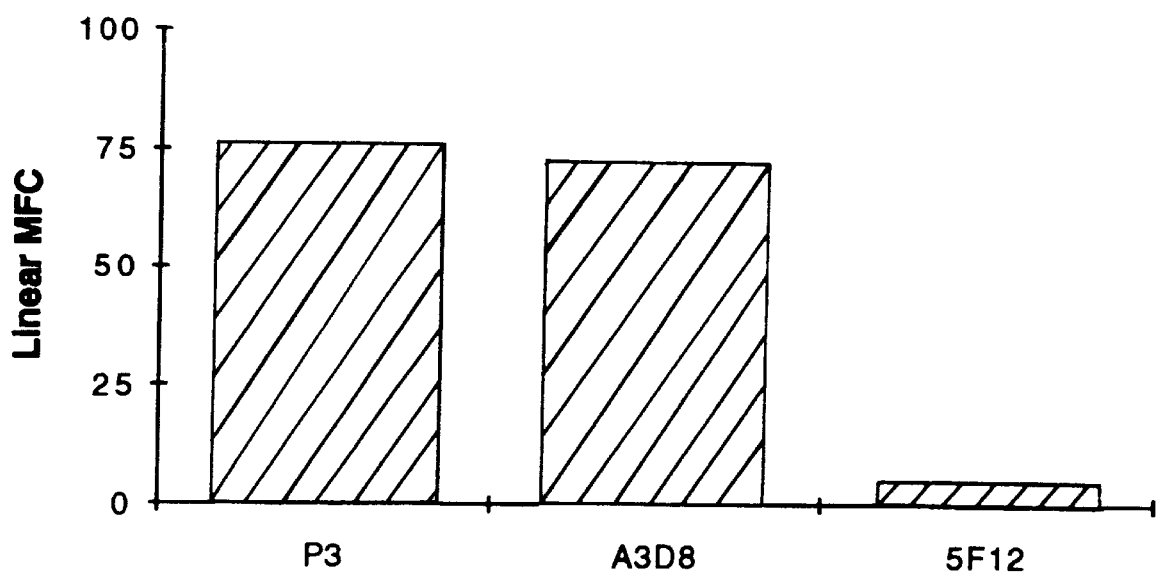
FIG. 12. Ability of CD44 mabs A3DB and 5F12 to block 5F112-FITC binding to CD44 on the CD44H transfected Jurkat T cells. Cells were incubated with 5 μg of the unlabelled mabs as indicated for 30 min at 4° C. followed by incubated with 3.5 μg of FITC labelled 5F12 IgG. Results were expressed as linear MFC analyzed by flow cytometry, and are representative of three separate experiments.

Inability of monoclonal antibodies A1G3 and A3D8 to block the binding of mab 5F12 to CD44H-transfectant Jurkat cells:

To determine if monoclonal antibody 5F12 bound to the same or to a different epitope than monoclonal antibodies A1G3 and A3D8, unlabelled mabs A3D8 and 5F12 were used to block the binding of directly fluoresceinated 5F12 (5F12 FITC) (FIG. 12). Unlabelled SF12 completely blocked the binding of 5F12-FITC to CD44H-transfectant Jurkat cells, while monoclonal antibody A3D8 did not block 5F12-FITC binding. These data suggested that 5F12 bound to a different epitope of CD44H than did monoclonal antibodies A1G3 and A3D8.

Figure 13:
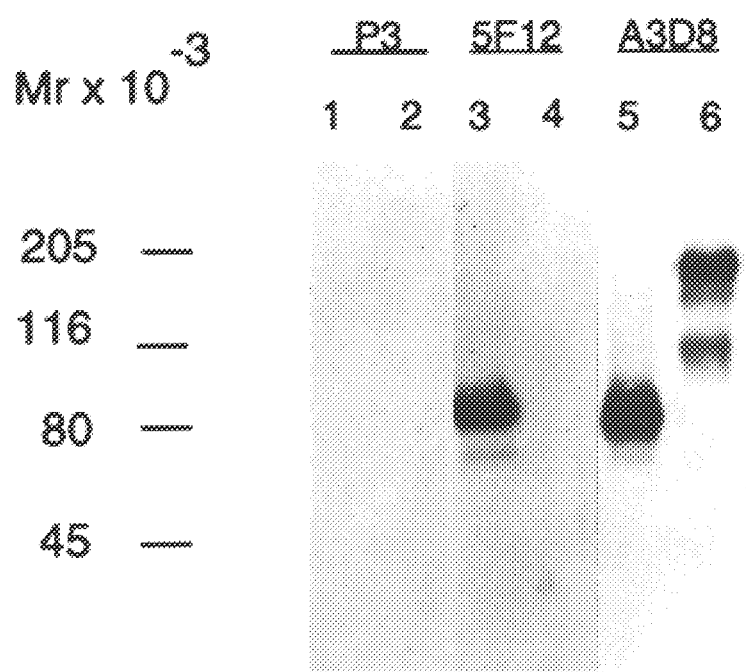
FIG. 13. Western blot analysis of reactivity of CD44 mabs with CD44 protein in CD44H transfected Jurkat T Cells and CD44-Rg. Cell lysates (approximately $1 \times 10^6$ cells/lane, lanes 2,4,6) and CD44-Rg (100 ng/lane, lanes 1,3,5) were run on a 7.5% SDS-PAGE under non-reducing conditions, followed by transfer to nitrocellulose membranes. The protein bands of CD44 were revealed by the indicated CD44 mabs. The P3 mab was used as a negative control.
Figure 14A:
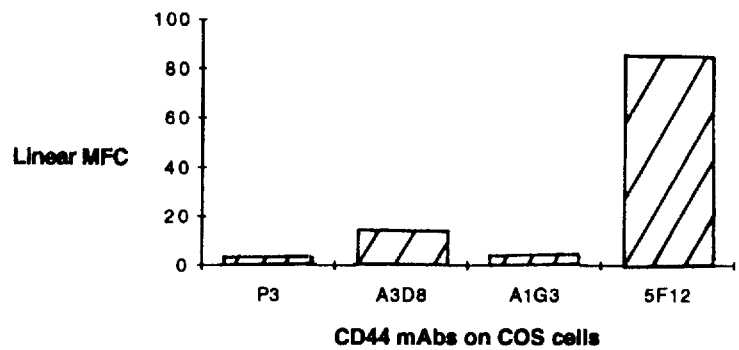
FIGS. 14A–C. Reactivity of CD44 mabs on human CD44 transfected Jurkat T cells, African Green Monkey cos cells and baboon 26 CB-1 cells. The indicated cells ($1 \times 10^6$ cells/sample) were incubated with 50 μl of CD44 mabs at the concentration of 7 μg/ml for purified S314, 5F12 and P3 IgG or at 1:300 dilution for ascites of S317, S318 and S324, followed by goat anti-mouse IgG labelled with FITC. Data are representative of three separate experiments.
Figure 14B:
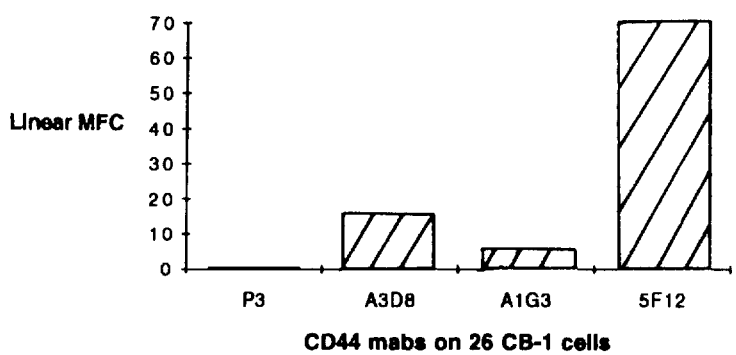
Figure 14C:
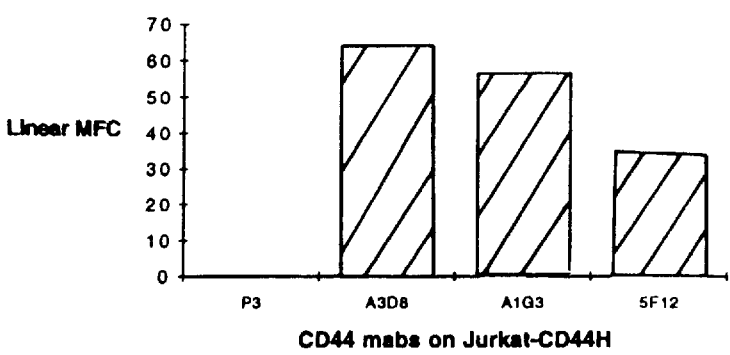

Ability of CD44 monoclonal antibodies to bind to various forms of CD44 molecules:

Monoclonal antibodies 5F12, A1G3 and A3DB were tested for their ability to bind to recombinant soluble CD44-Rg fusion protein produced by CD44 Rg-transfected African Green monkey cos cells (Liao et al, J. Immunol. in press (1993)). In the CD44-Rg cDNA, Seed et al deleted the first 20 amino acids at the N-terminus of CD44 and substituted 5 amino acids of the leader sequence of CD5 in order to optimize expression of the CD44-Rg fusion molecule (Liao et al, J. Immunol. in press (1993)). Interestingly, whereas mab A3D8 immunoblotted the CD44-Rg recombinant protein as well as cell surface CD44H from Jurkat cells, mab 5F12 only reacted in Western blot assay with cell surface CD44H from CD44-transfected Jurkat cells, but did not react with soluble CD44-Rg fusion protein (FIG. 13). Next, the ability of mabs A1G3, A3D8 and 5F12 to bind to endogenous African Green monkey kidney cell CD44 expressed on cos cells, to bind to baboon CD44 expressed on 26 CB-1 cells, or to bind to human CD44H transfected Jurkat cells was determined by indirect immunofluorescence and flow cytometry. FIG. 14 shows that only 5F12 reacted well with cos cells and 26 CB-1 cells, while all 3 mabs reacted well with human CD44H in Jurkat T cells.

N-Terminal sequence analysis of CD44 molecules from different sources:

Table 11 shows the N-terminal seqeunce of endogenous cos cell Africal Green Monkey CD44, human CD44 and the CD44-Rg fusion protein. In Table 11, the N-terminal amino acids of CD44 are predicted to begin at the sequence MDKFWW (SEQ ID NO:23) and the RLRVP (SEQ ID NO:24) sequence is derived from the CD5 molecule (Liao et al, J. Immunol. in press (1993)). Because mAb 5F12 blocks HA binding and binds to cos cell CD44, binds to human Jurkat CD44H-transfected CD44, but does not bind to the CD44-Rg fusion protein, these data demonstrate that one region of CD44H involved in HA binding and defined by mAb SF12 consists of amino acids centering around the N-terminal initial 42 amino acids of CD44 (MDKFWWHAAWGLCLVPLSLAQIDLNTCRFAGVF HVEKNGRY) (SEQ ID NO:25) with the 5F12 mab binding site requiring the presence of amino acids 1–20 of CD44.

TABLE 11

N-terminal Sequences of Various CD44

| Name of CD44 | Amino Acid Sequence | Information Source |
|---|---|---|
| Cos CD44 (African Green Monkey) | MDKFWWHAAWGLCLLQLSLAQIDLN (SEQ ID NO:26) | cDNA |
| Human CD44H | MDKFWWHAAWGLCLVPLSLAQIDLN (SEQ ID NO:27) | cDNA |
| CD44-Rg | RLRVPQIDLN (SEQ ID NO:28) | Protein |

The N-terminal aa sequence of African Green monkey CD44 and human CD44H were deduced from the corresponding cDNAs as described. The N-terminal amino acid sequence of CD44-Rg were determined by the N-terminal amino acid sequencing of CD44-Rg as described. Amino acids underlined are different in comparison with human CD44H. The underlined aa sequence of CD44-Rg is from CD5 (Miyake et al, J. Exp. Med. 172:69 (1990)). CD44-Rg is a fusion protein of the extracellular domain of CD44 (minus the N-terminal aa 1–20) and the hinge, CH2 and CH3 regions of human IgG1 (Miyake et al, J. Exp. Med. 172:69 (1990)).

The data demonstrate that amino acids 1–21 are required for mab 5F12 binding to CD44 and that these amino acids are likely involved in HA binding to CD44 in addition to amino acids 21–45. Taken together with the findings of Peach et al (J. Cell Biol. 1222:257 (1993)), the data indicate that peptides within amino acids 1–42 (amino acids 1–20 and CD44-9 peptide, Table 1) and peptides within amino acids 150–167 (CD44-3, CD44-4, CD44-4, CD44-5 and CD44-8 peptides, Table 1) are involved in HA binding, and therefore will, in and of themselves, be of use as therapeutic agents to block HA binding to CD44H or CD44E. He et al (J. Cell. Biol. 119:1711) and Liao et al (J. Immunol. Dec. 1, 1993) have both shown that CD44H and CD44E can bind HA.

All documents referenced hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims. For example, one skilled in the art will appreciate that the peptides of the invention can be present alone or any two or more can by synthesized together as a single peptide and used in that form.

Hybridoma 5F12, clone 4, was deposited at the American Type Culture Collection, 12301 Parklawn Drive, Rockville, Md. 20852 and was given ATCC Deposit No. HB11480 on Oct. 28, 1993.

What is claimed is:

1. A method of suppressing T cell activation in a mammal comprising administering to said mammal a CD44 peptide having an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12. SEQ ID NO:13, SEQ ID NO:14, SEQ ID NO:15 and SEQ ID NO:16, in an amount sufficient to suppress said T cell activation.

2. A method of inhibiting CD44-mediated cell adhesion or CD44-monocyte interleukin-1 release in a mammal comprising administering to said mammal a CD44 peptide having an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9. SEQ ID NO:10, SEQ ID NO:11. SEQ ID NO:12, SEQ ID NO:13, SEQ ID NO:14, SEQ ID NO:15 and SEQ ID NO:16, in an amount sufficient to inhibit said CD44-mediated cell adhesion or CD44-monocyte IL1 release.

3. A method of treating inflammation in a mammal comprising administering to said mammal a CD44 peptide having an amino acid sequence selected from the group consisting of SEQ ID NO:1, SEQ ID NO:2, SEQ ID NO:3, SEQ ID NO:4, SEQ ID NO:5, SEQ ID NO:6. SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15 and SEQ ID NO:16, in an amount sufficient to reduce said inflammation.

4. The method according to any one of claims 1–3 wherein said peptide has the amino acid sequence of SEQ ID NO:7.

5. A method of treating a hematopoietic malignancy comprising administering to a mammal in need of such treatment a peptide having the amino acid sequence of SEQ ID NO:7 in an amount sufficient to effect said treatment.

6. A peptide having the amino acid sequence of SEQ ID NO:7.

7. A peptide having an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15 and SEQ ID NO:16.

8. A method of inhibiting binding of hyaluronan to a molecule of CD44 comprising contacting said molecule of CD44 with at least one peptide having an amino acid sequence selected from the group consisting of SEQ ID NO:3, SEQ ID NO:4, SEQ ID NO:5, SEQ ID NO:8, SEQ ID NO:9 and SEQ ID NO:10, under conditions such that said binding is inhibited.

9. A peptide having the amino acid sequence of SEQ ID NO:10.

10. A pharmaceutical composition comprising the peptide according to claim 7 and a pharmaceutically acceptable carrier.

11. The method according to any one of the claims 1–3 wherein said CD44 peptide is administered topically to said mammal.

12. The method according to claim 8 wherein said peptide has the amino acid sequence of SEQ ID NO:10.

13. A method of inhibiting binding of hyaluron on to a molecule of CD44 comprising contacting said molecule of CD44 with a peptide having the amino acid sequence of SEQ ID NO:7 and with at least one peptide having an amino acid sequence selected from the group consisting of SEQ ID NO:3, SEQ ID NO:4, SEQ ID NO:5, SEQ ID NO:8, SEQ ID NO:9 and SEQ ID NO:10, under conditions such that said binding is inhibited.

* * * * *